(12) United States Patent
Yamanoi et al.

(10) Patent No.: US 8,754,112 B2
(45) Date of Patent: Jun. 17, 2014

(54) SULFONE DERIVATIVE

(75) Inventors: Shigeo Yamanoi, Kanagawa (JP); Hidenori Namiki, Kanagawa (JP); Takahiro Katagiri, Tokyo (JP); Mayuko Akiu, Tokyo (JP); Katsuji Kagechika, Tokyo (JP); Takeshi Honda, Tokyo (JP); Koji Matsumoto, Tokyo (JP); Ryutaro Nakashima, Kanagawa (JP)

(73) Assignee: Daiichi Sankyo Company, Limited, Chuo-ku (JP)

( * ) Notice: Subject to any disclaimer, the term of this patent is extended or adjusted under 35 U.S.C. 154(b) by 109 days.

(21) Appl. No.: 13/388,218

(22) PCT Filed: Aug. 4, 2010

(86) PCT No.: PCT/JP2010/063150
§ 371 (c)(1),
(2), (4) Date: Jan. 31, 2012

(87) PCT Pub. No.: WO2011/016470
PCT Pub. Date: Feb. 10, 2011

(65) Prior Publication Data
US 2012/0129891 A1  May 24, 2012

(30) Foreign Application Priority Data
Aug. 5, 2009 (JP) ................................. 2009-182721

(51) Int. Cl.
*A61K 31/4245* (2006.01)
*C07D 271/06* (2006.01)

(52) U.S. Cl.
USPC ......................... 514/364; 548/131

(58) Field of Classification Search
USPC ........................................... 548/131; 514/364
See application file for complete search history.

(56) References Cited

FOREIGN PATENT DOCUMENTS

| WO | 97/46556 A1 | 12/1997 |
|----|-------------|---------|
| WO | 2005/061489 A1 | 7/2005 |
| WO | 2007/003960 A1 | 1/2007 |
| WO | 2007/003962 A2 | 1/2007 |
| WO | 2007/116229 A1 | 10/2007 |

OTHER PUBLICATIONS

Poradzka et al., Insulin Replacement Therapy, etc., Acta Poloniae Pharmaceutica-Drug Research, 70 (6), pp. 943-950, 2013.*
Kawasaki, "Prevention of type 1, etc.," Medline 2004591180, 2005.*
Meier, "Beta cell mass, etc.," Diabetologia (2008) 51:703-713.*
Martinic et al., "Real-time imaging, etc.," Immunological Reviews 2008, 22: 200-213.*
Hanley, "Pancreatic beta-cell, etc.," McGill Journal of Medicine, 2009 12(2): 51-60.*
Blake et al., "Mitochondrial dysfunction, etc.," Biochim. Biophys. Acta (2013) pp. 1-9, http://dx.doi.org/j.bbagen.2013.11.007.*
International Search Report mailed Sep. 7, 2010, issued in corresponding International Application No. PCT/JP2010/063150, filed Aug. 4, 2010, 2 pages.

* cited by examiner

*Primary Examiner* — Patricia L Morris
(74) *Attorney, Agent, or Firm* — Christensen O'Connor Johnson Kindness PLLC

(57) ABSTRACT

Provided are a compound having an excellent hypoglycemic action, or a pharmaceutically acceptable salt thereof, and a pharmaceutical composition having an excellent therapeutic effect and/or prophylactic effect on type 1 diabetes, type 2 diabetes, and the like, which cause an increase in the blood sugar level due to abnormal sugar metabolism. A compound represented by general formula (I), or a pharmaceutically acceptable salt thereof, is disclosed.

17 Claims, No Drawings

SULFONE DERIVATIVE

TECHNICAL FIELD

The present invention relates to a novel sulfone derivative having a hypoglycemic action and/or a β cell- or pancreas-protecting action, or a pharmaceutically acceptable salt thereof, and to a pharmaceutical composition containing these as active ingredients.

BACKGROUND ART

Diabetes mellitus is a metabolic disease primarily characterized by a chronic hyperglycemic state due to a lack of insulin action. The treatment of diabetes is generally by drug therapy together with diet therapy and exercise therapy. Examples of oral hypoglycemic agents in use, which are a class of therapeutic drugs for diabetes, include biguanide agents and thiazolidinedione agents that improve insulin resistance; sulfonylurea agents and glinide drugs that promote insulin secretion from pancreatic β cells; and α-glucosidase inhibitors that inhibit sugar absorption.

However, it is reported that biguanide agents have adverse side effects such as digestive symptoms and lactic acidosis; thiazolidinedione agents have adverse side products such as weight gain and edema; sulfonylurea agents and glinide drugs have adverse side effects such as hypoglycemia or secondary failure due to long-term use; and α-glucosidase inhibitors have adverse side effects such as diarrhea. Therefore, development of an oral hypoglycemic agent which can address such problems is desired.

Furthermore, in recent years, piperidine compounds have been developed as oral hypoglycemic agents having new structures (see, for example, Patent Literatures 1 to 4).

CITATION LIST

Patent Literature

Patent Literature 1: WO 07/116,229
Patent Literature 2: WO 07/003,960
Patent Literature 3: WO 07/003,962
Patent Literature 4: WO 05/061489

SUMMARY OF THE INVENTION

Technical problem

However, the compounds described in the above-described patent literatures have a problem in that a sufficient hypoglycemic action and a β cell- or pancreas-protecting action cannot be easily obtained. Furthermore, the patent literatures described above disclose compounds containing a cyclohexane ring or a piperidine ring in their structures, but neither describe nor suggest any compounds containing a benzene ring, a pyridine ring or a pyridazine ring in their structures, instead of a cyclohexane ring or a piperidine ring. Thus, an object of the present invention is to provide compounds which have a new structure that is neither described nor suggested in the above patent literatures and has an excellent hypoglycemic action and a β cell- or pancreas-protecting action, or a pharmaceutically acceptable salt thereof; a pharmaceutical composition having an excellent therapeutic effect and/or prophylactic effect on type 1 diabetes, type 2 diabetes and the like, which cause an increase in the blood sugar level due to abnormal sugar metabolism; and a pharmaceutical composition having a β cell- or pancreas-protecting action.

Solution to Problem

The present invention provides:
(1) A compound represented by general formula (I):

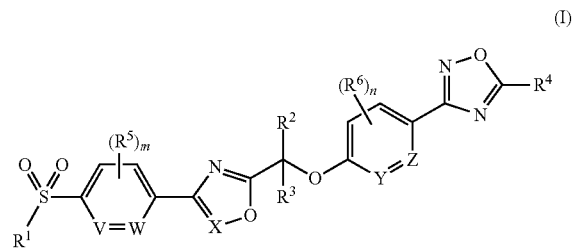

wherein $R^1$ represents a C1-C6 alkyl group;
$R^2$ and $R^3$ each independently represent a hydrogen atom or a C1-C6 alkyl group;
$R^4$ represents a C1-C6 alkyl group;
$R^5$ and $R^6$ each independently represent a halogen atom or a C1-C6 alkyl group;
m and n each independently represent an integer from 0 to 4; and
V, W, X, Y and Z each independently represent CH or N, or a pharmaceutically acceptable salt thereof;
(2) the compound as set forth in item (1), wherein Y and Z both represent CH; (3) the compound as set forth in item (1) or (2), wherein V and W both represent CH;
(4) the compound as set forth in any one of items (1) to (3), wherein X represents N;
(5) the compound as set forth in any one of items (1) to (4), wherein $R^2$ represents a C1-C3 alkyl group;
(6) the compound as set forth in any one of items (1) to (4), wherein $R^1$ represents a methyl group;
(7) the compound as set forth in any one of items (1) to (6), wherein $R^2$ represents a hydrogen atom or a C1-C3 alkyl group;
(8) the compound as set forth in any one of items (1) to (6), wherein $R^2$ represents a hydrogen atom, a methyl group, an ethyl group, a propyl group or an isopropyl group;
(9) the compound as set forth in any one of items (1) to (8), wherein $R^3$ represents a hydrogen atom or a C1-C3 alkyl group;
(10) the compound as set forth in any one of items (1) to (8), wherein $R^3$ represents a hydrogen atom or a methyl group;
(11) the compound as set forth in any one of items (1) to (10), wherein $R^4$ represents a C1-C3 alkyl group;
(12) the compound as set forth in any one of items (1) to (10), wherein $R^4$ represents an ethyl group, an isopropyl group or a tert-butyl group;
(13) the compound as set forth in any one of items (1) to (12), wherein $R^5$ represents a halogen atom or a C1-C3 alkyl group, and m represents 1;
(14) the compound as set forth in any one of items (1) to (12), wherein $R^5$ represents a fluorine atom or a methyl group, and m represents 1;
(15) the compound as set forth in any one of items (1) to (14), wherein $R^6$ represents a C1-C3 alkyl group, and n represents 1;
(16) the compound as set forth in any one of items (1) to (14), wherein n represents 0;

(17) a compound selected from the group consisting of the following compounds:

3-[3-fluoro-4-methylsulfonyl]phenyl]-5-{1-[4-(5-isopropyl-1,2,4-oxadiazol-3-yl)phenoxy]propyl}-1,2,4-oxadiazole;
3-[3-fluoro-4-methylsulfonyl]phenyl]-5-{1-[4-(5-isopropyl-1,2,4-oxadiazol-3-yl)phenoxy]ethyl}-1,2,4-oxadiazole;
3-[3-fluoro-4-(methylsulfonyl)phenyl]-5-{1-[4-(5-isopropyl-1,2,4-oxadiazol-3-yl)phenoxy]butyl}-1,2,4-oxadiazole;
5-ethyl-3-[4-(1-{3-[3-fluoro-4-(methylsulfonyl)phenyl]-1,2,4-oxadiazol-5-yl}propyl)phenyl]-1,2,4-oxadiazole;
5-(1-{3-[3-fluoro-4-(methylsulfonyl)phenyl]-1,2,4-oxadiazol-5-yl}propoxy)-2-(5-isopropyl-1,2,4-oxadiazol-3-yl)pyridine;
3-[4-(1-{4-[3-fluoro-4-(methylsulfonyl)phenyl]-1,3-oxazol-2-yl}propoxy)phenyl]-5-isopropyl-1,2,4-oxadiazole;
3-[3-fluoro-4-(methylsulfonyl)phenyl]-5-{(1R)-1-[4-(5-isopropyl-1,2,4-oxadiazol-3-yl)phenoxy]propyl}-1,2,4-oxadiazole; and
5-ethyl-3-(4-{[(1R)-1-{3-[3-fluoro-4-(methylsulfonyl)phenyl]-1,2,4-oxadiazol-5-yl}propyl]oxy}phenyl)-1,2,4-oxadiazole;

or a pharmaceutically acceptable salt thereof,

(18) a pharmaceutical composition comprising, as an active ingredient, the compound as set forth in any one of items (1) to (17), or a pharmaceutically acceptable salt thereof;

(19) the pharmaceutical composition as set forth in item (18), for treating and/or preventing type 1 diabetes, type 2 diabetes, a diabetes-associated disease, or obesity;

(20) the pharmaceutical composition as set forth in item (18), for protecting β cells or the pancreas;

(21) use of the compound as set forth in any one of items (1) to (17) or a pharmaceutically acceptable salt thereof, for preparing a pharmaceutical composition;

(22) a method for treating and/or preventing a disease, the method including administering to a mammal a pharmacologically effective amount of the compound as set forth in any one of items (1) to (17) or a pharmaceutically acceptable salt thereof;

(23) the method as set forth in item (22), wherein the disease is type 1 diabetes, type 2 diabetes, a diabetes-associated disease, or obesity;

(24) a method for protecting β cells or pancreas, the method including administering to a mammal a pharmacologically effective amount of the compound as set forth in any one of items (1) to (17) or a pharmaceutically acceptable salt thereof; and

(25) the method as set forth in any one of items (22) to (24), wherein the mammal is a human being.

Advantageous Effects of Invention

According to the present invention, there can be provided a sulfone compound having an excellent hypoglycemic action or a pharmaceutically acceptable salt thereof, and a pharmaceutical composition having an excellent therapeutic effect and/or prophylactic effect for type 1 diabetes, type 2 diabetes and the like, which cause an increase in the blood sugar level.

DESCRIPTION OF EMBODIMENTS

A "C1-C6 alkyl group" as used in the present specification means a linear, branched or cyclic alkyl group having 1 to 6 carbon atoms. Specific examples include a methyl group, an ethyl group, a propyl group, an isopropyl group, a cyclopropyl group, a butyl group, an isobutyl group, a sec-butyl group, a tert-butyl group, a pentyl group, a 1,2-dimethylpropyl group, an isopentyl group, a hexyl group, and an isohexyl group.

A "halogen atom" as used in the present specification means a fluorine atom, a chlorine atom, a bromine atom or an iodine atom.

A "pharmaceutically acceptable salt" as used in the present specification means a salt that is formed by allowing the compound of the present invention to react with an acid or a base.

Examples of the salt include hydrohalogenic acid salts such as hydrofluorides, hydrochlorides, hydrobromides, and hydroiodides; inorganic acid salts such as hydrochlorides, nitrates, perchlorates, sulfates and phosphates; lower alkanesulfonic acid salts such as methanesulfonates, trifluoromethanesulfonates, and ethanesulfonates;

arylsulfonic acid salts such as benzenesulfonates, and p-toluenesulfonates; organic acid salts such as acetates, malates, fumarates, succinates, citrates, ascorbates, tartrates, oxalates, and maleates; alkali metal salts such as sodium salts, potassium salts, and lithium salts; alkaline earth metal salts such as calcium salts and magnesium salts; metal salts such as aluminum salts and iron salts; inorganic salts such as ammonium salts; amine salts including organic salts such as t-octylamine salts, dibenzylamine salts, morpholine salts, glucosamine salts, phenylglycine alkyl ester salts, ethylenediamine salts, N-methylglucamine salts, guanidine salts, diethylamine salts, triethylamine salts, dicyclohexylamine salts, N,N'-dibenzylethylenediamine salts, chloroprocaine salts, procaine salts, diethanolamine salts, N-benzylphenethylamine salts, piperazine salts, tetramethylammonium salts, and tris(hydroxymethyl)aminomethane salts; and amino acid salts such as glycine salts, lysine salts, arginine salts, ornithine salts, glutamates, and aspartates.

The compound of the present invention absorbs water when, for example, left to stand in the atmosphere or the like, so that adsorbed water may adhere to the compound and a hydrate may be formed. Therefore, such hydrates are also included in the concept of the salt of the present invention.

Since the compound of the present invention may have asymmetric carbon atoms in the molecule, the compound has optical isomers. These isomers and mixtures of these isomers are all represented by a single formula, that is, the general formula (I). Therefore, the present invention encompasses all of the optical isomers of the compound represented by the general formula (I), and mixtures of these optical isomers in any ratios. Such an optical isomer can be produced by, for example, using raw materials having optical activity instead of the raw materials used in the production methods, Reference Examples and Examples that will be described below, or can be obtained by subjecting a compound that has been produced by making reference to the production methods, Reference Examples, Examples and the like that will be described below, to an optical resolution method that is known in the relevant art, for example, a diastereomer method, an enzymatic reaction method, or an optical resolution method based on chromatography.

The present invention may also encompass compounds in which one or more of the atoms constituting the compound represented by the general formula (I) have been substituted with isotopes of the atoms. Isotopes include two classes such as radioactive isotopes and stable isotopes, and examples of the isotopes include, for example, isotopes of hydrogen ($^{2}$H and $^{3}$H), isotopes of carbon ($^{11}$C, $^{13}$C and $^{14}$C), isotopes of nitrogen ($^{13}$N and $^{15}$N), isotopes of oxygen ($^{15}$O, $^{17}$O and $^{18}$O), and isotopes of fluorine ($^{18}$F). A composition containing a compound labeled with an isotope is useful as, for example, a therapeutic agent, a prophylactic agent, a research reagent, an assay reagent, a diagnostic agent, or an in vivo diagnostic imaging agent. Compounds labeled with isotopes and mixtures of compounds labeled with isotopes in any ratios are all included in the present invention. A compound labeled with an isotope can be produced by methods known in the relevant art, for example, using raw materials labeled with isotopes instead of the raw materials used in the production methods of the present invention that will be described below.

The present invention may also encompass prodrugs of the compound represented by the general formula (I). A prodrug is a derivative of the compound represented by the general formula (I), and means a compound which is enzymatically or chemically converted to the compound of the present invention in the living body.

Examples of the prodrug include compounds in which an amino group in the molecule has been acylated, alkylated or phosphorylated; compounds in which a carboxyl group in the molecule has been esterified or amidated; and compounds in which a hydroxyl group in the molecule has been acylated, alkylated or phosphorylated (see, for example, Povl Krogsgaard-Larsen, et al., "A Textbook of Drug Design and Development", Second Edition, Harwood Academic Publishers, 1996, pp. 351-385). Such a prodrug can be produced from the compound represented by the general formula (I) by methods known in the relevant art.

V preferably represents CH.
W preferably represents CH.
X preferably represents N.
Y preferably represents CH.
Z preferably represents CH.
$R^1$ preferably represents a C1-C3 alkyl group; and more preferably a methyl group.
$R^2$ preferably represents a hydrogen atom or a C1-C3 alkyl group; more preferably a hydrogen atom, a methyl group, an ethyl group, a propyl group or an isopropyl group; and even more preferably an ethyl group.
$R^3$ preferably represents a hydrogen atom or a C1-C3 alkyl group; more preferably a hydrogen atom or a methyl group; and even more preferably a hydrogen atom.
$R^4$ preferably represents a C1-C3 alkyl group; more preferably an ethyl group, an isopropyl group or a tert-butyl group; and even more preferably an isopropyl group.
$R^5$ preferably represents a halogen atom or a C1-C3 alkyl group; more preferably a fluorine atom or a methyl group; and even more preferably a fluorine atom.
$R^6$ preferably represents a C1-C3 alkyl group; and more preferably a methyl group.
m preferably represents 0 or 1; and more preferably 1.
n preferably represents 0 or 1; and more preferably 0.

A preferred combination of V, W, X, Y, Z, $R^1$, $R^2$, $R^3$, $R^4$, $R^5$, $R^6$, m and n in the general formula (I) is the combination in which V is CH; W is CH; X is N; Y is CH; Z is CH; $R^1$ and $R^4$ are each independently a C1-C3 alkyl group; $R^2$ and $R^3$ are each independently a hydrogen atom or a C1-C3 alkyl group; $R^5$ is a halogen atom or a C1-C3 alkyl group; $R^6$ is a C1-C3 alkyl group; m is 0 or 1; and n is 0 or 1.

A more preferred combination is the combination in which V is CH; W is CH; X is N; Y is CH; Z is CH; $R^4$ is a methyl group; $R^2$ is a hydrogen atom, a methyl group, an ethyl group, a propyl group or an isopropyl group; $R^3$ is a hydrogen atom or a methyl group; $R^4$ is an ethyl group, an isopropyl group or a tert-butyl group; $R^5$ is a fluorine atom or a methyl group; m represents 1; and n represents 0.

The compound of the present invention can be produced by, for example, the following methods A to C. In addition, for the benzene-based compounds, pyridine-based compounds, pyridazine-based compounds or amino-based compounds that are used as the starting raw materials in the following production methods, commercially available compounds can be used.

Method A is a method for producing a compound (Ia) of the present invention represented by the general formula (I), in which X is N.

Method B is a method for producing a compound (Ib) of the present invention represented by the general formula (I), in which X is CH.

In the reactions of the various steps of the methods described below, when a compound serving as a reaction substrate has a group which inhibits the intended reaction (for example, a hydroxyl group, or a carboxyl group), introduction of a protective group to such a group and removal of the introduced protective group may be carried out as necessary. There are no particular limitations on these protective groups as long as they are conventionally used protective groups, but examples include those protective groups described in T. H. Greene, P. G. Wuts, Protective Groups in Organic Synthesis. Third Edition, 1999, John Wiley & Sons, Inc., or the like. The reaction for introducing these protective groups and the reaction for removing the protective groups can be carried out according to routine methods, such as the methods described in the literature mentioned above.

Explanations of the various steps in method A and method B will be described below.

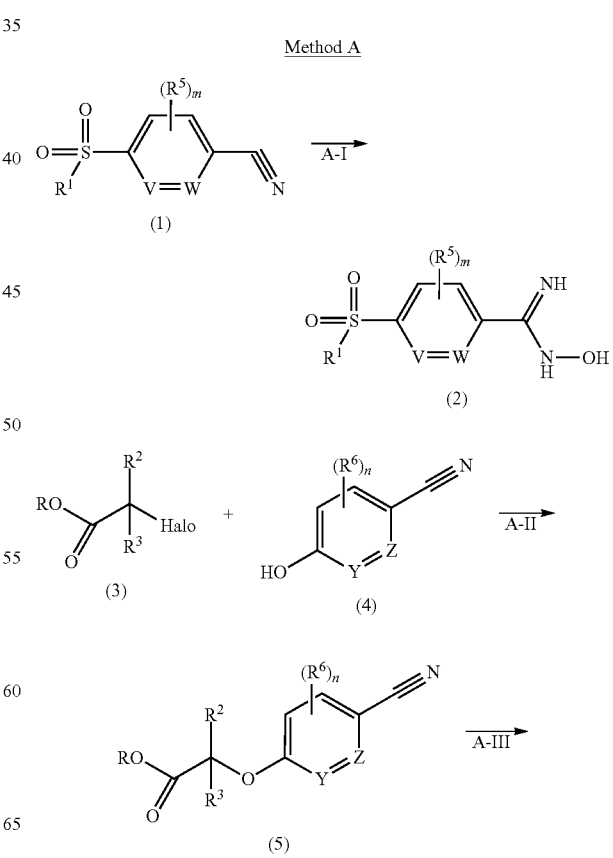

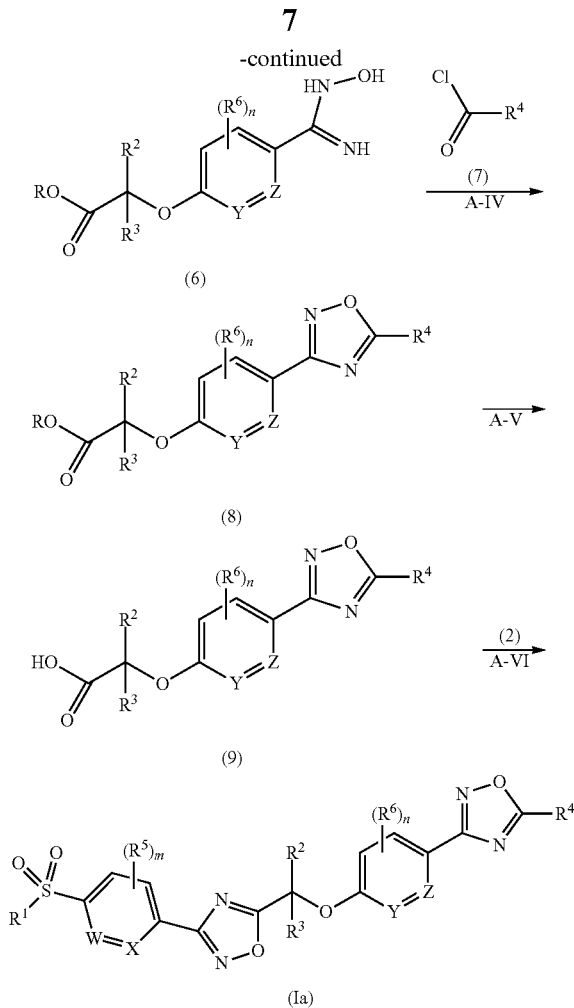

wherein R represents a protective group for a carboxyl group; Halo represents a halogen atom; and V, W, Y, Z, $R^1$, $R^2$, $R^3$, $R^4$, $R^5$, $R^6$, m and n respectively have the same meanings as defined above.

Step A-I is a step for producing a compound (2) by allowing a compound (1) to react with hydroxylamine.

Examples of a solvent used therein include methanol, ethanol, a methanol/toluene mixed solvent, dimethylformamide (DMF) and dimethyl sulfoxide, and a preferred example is ethanol.

Examples of hydroxylamine used therein include a 50 w/w % aqueous solution of hydroxylamine and hydroxylamine hydrochloride, and a preferred example is a 50 w/w % aqueous solution of hydroxylamine.

Examples of a reagent used therein include sodium carbonate, potassium carbonate, cesium carbonate, potassium tert-butoxide, triethylamine, and diisopropylethylamine.

The reaction temperature is 0° C. to 150° C., and preferably 50° C. to 100° C. The reaction time is 10 minutes to 24 hours, and preferably 30 minutes to 5 hours.

When a workup is needed, the workup may be carried out according to the following procedure, for example. The reaction mixture is cooled to room temperature, subsequently the solvent is distilled off under reduced pressure, and the resulting residue is washed with hexane.

Step A-II is a step for producing a compound (5) by allowing a compound (3) to react with a compound (4) in the presence of a base.

Examples of a solvent used therein include tetrahydrofuran (THF), 1,4-dioxane, acetonitrile, acetone and DMF, and a preferred example is acetonitrile.

Examples of the base used therein include sodium carbonate, potassium carbonate, cesium carbonate, potassium tert-butoxide and sodium hydroxide, and a preferred example is potassium carbonate.

The reaction temperature is 0° C. to 150° C., and preferably 20° C. to 130° C. The reaction time is 30 minutes to 24 hours, and preferably 30 minutes to 6 hours.

When a workup is needed, the workup may be carried out according to the following procedure, for example. The reaction mixture is cooled to room temperature, and then the insoluble matter is removed by using Celite. The solvent is distilled off under reduced pressure from the reaction mixture from which the insoluble matter has been removed. The resulting residue is purified by silica gel chromatography, or is washed with an organic solvent, water or the like.

Step A-III is a step for producing a compound (6) by allowing the compound (5) obtained in step A-II to react with hydroxylamine.

Examples of a solvent used therein include the same solvents as the solvents used in step A-I, and a preferred example is ethanol.

Examples of hydroxylamine used therein include the same hydroxylamines as the hydroxylamines used in step A-I, and a preferred example is a 50 w/w % aqueous solution of hydroxylamine.

Examples of a reagent used therein include the same reagents as the reagents used in step A-I.

The reaction temperature is 0° C. to 150° C., and preferably 50° C. to 100° C. The reaction time is 10 minutes to 24 hours, and preferably 30 minutes to 5 hours.

When a workup is needed, the workup may be carried out according to the following procedure, for example. The reaction mixture is cooled to room temperature, subsequently the solvent is distilled off under reduced pressure, and the resulting residue is washed with hexane.

Step A-IV is a step for producing a compound (8) by allowing the compound (6) obtained in step A-III to react with an acid halide (7).

Examples of a solvent used therein include THF, DMF, toluene and pyridine, and a preferred example is pyridine.

Examples of a reagent used therein include pyridine, triethylamine, diisopropylethylamine, and sodium hydride.

The reaction temperature is 20° C. to 150° C., and preferably 40° C. to 100° C. The reaction time is 30 minutes to 24 hours, and preferably 30 minutes to 10 hours.

When a workup is needed, the workup may be carried out according to the following procedure, for example. A saturated ammonium chloride solution, water or saturated brine is added to the reaction mixture, the product is extracted using an organic solvent such as ethyl acetate, and the organic layer thus obtained is dried over sodium sulfate. After the insoluble matter is removed, the solvent is distilled off under reduced pressure.

Step A-V is a step for producing a compound (9) by hydrolyzing the compound (8) obtained in step A-IV.

Examples of a solvent used therein include THF, methanol, ethanol and isopropyl alcohol, and a preferred example is methanol.

Examples of a reagent used therein include an aqueous solution of sodium hydroxide, an aqueous solution of potassium hydroxide and an aqueous solution of lithium hydroxide, and a preferred example is an aqueous solution of sodium hydroxide.

The reaction temperature is 0° C. to 130° C., and preferably 20° C. to 70° C. The reaction time is 30 minutes to 12 hours, and preferably 30 minutes to 4 hours.

When a workup is needed, the workup may be carried out according to the following procedure, for example. An acid such as hydrochloric acid is added to the reaction mixture to make the reaction mixture acidic or neutral, and the product is extracted using an organic solvent such as ethyl acetate. The organic layer thus obtained is dried over a desiccant such as sodium sulfate. The insoluble matter is removed, and then the solvent is distilled off under reduced pressure.

Step A-VI is a step for producing a compound (1a) by allowing the compound (2) obtained in step A-I to react with the compound (9) obtained in step A-V.

Examples of a solvent used therein include 3-dimethyl-2-imidazolidinone, and DMF.

Examples of a reagent used therein include 1-(3-dimethylaminopropyl)-3-ethylcarbodiimide, and 1-hydroxybenzotriazole.

The reaction temperature is 30° C. to 130° C., and preferably 50° C. to 110° C. The reaction time is 30 minutes to 12 hours, and preferably 30 minutes to 6 hours.

When a workup is needed, the workup may be carried out according to the following procedure, for example. Water is added to the reaction mixture, and then the product is extracted using an organic solvent such as ethyl acetate. The organic layer thus obtained is washed with water, saturated brine or the like, and is dried over a desiccant such as sodium sulfate. The solvent is distilled off under reduced pressure, and the residue is purified by silica gel chromatography.

Method B

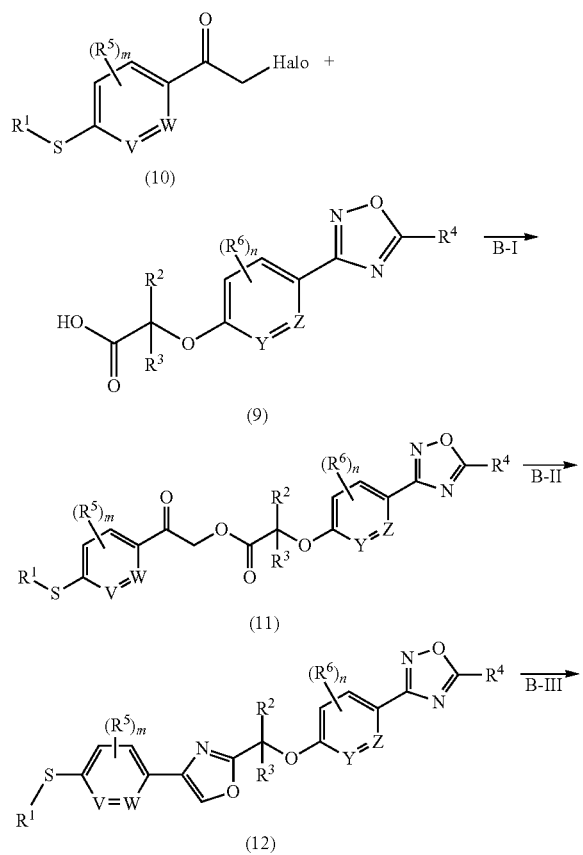

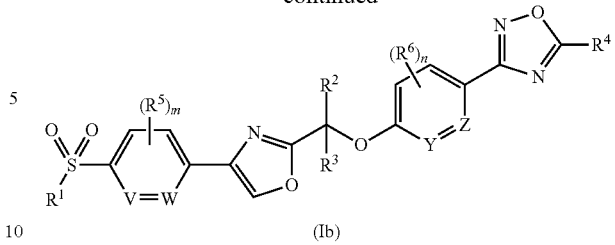

(Ib)

wherein Halo, V, W, Y, Z, $R^1$, $R^2$, $R^3$, $R^4$, $R^5$, $R^6$, m and n respectively have the same meanings as defined above.

Step B-I is a step for producing a compound (11) by reacting the compound (9) obtained in step A-V described above, with a compound (10).

Examples of a solvent used therein include THF, DMF, 1,4-dioxane, acetonitrile and acetone, and a preferred example is DMF or acetone.

Examples of a reagent used therein include potassium tert-butoxide, cesium carbonate, potassium carbonate, sodium carbonate, sodium hydride, triethylamine and diisopropylethylamine, and a preferred example is triethylamine.

The reaction temperature is 0° C. to 100° C., and preferably 20° C. to 80° C. The reaction time is 30 minutes to 24 hours, and preferably 30 minutes to 6 hours.

When a workup is needed, the workup may be carried out according to the following procedure, for example. Water is added to the reaction mixture, and the mixture is subjected to extraction with an organic solvent such as ethyl acetate. The organic layer thus obtained is washed sequentially with water and saturated brine. Subsequently, the organic layer is dried over a desiccant such as sodium sulfate or anhydrous sodium sulfate, and then the resulting residue is purified by silica gel chromatography.

Step B-II is a step for producing a compound (12) by cyclizing the compound (11) obtained in step B-I.

Examples of a solvent used therein include toluene and acetic acid.

Examples of a reagent used therein include ammonium trifluoroacetate and ammonium acetate, and a preferred example is ammonium trifluoroacetate.

The reaction temperature is 80° C. to 200° C., and preferably 100° C. to 160° C. The reaction time is 30 minutes to 24 hours, and preferably 30 minutes to 12 hours.

When a workup is needed, for example, a workup may be carried out according to step B-1.

Step B-III is a step for producing a compound (1b) by oxidizing the compound (12) obtained in step B-II.

Examples of a solvent used therein include dichloromethane, dichloroethane and chloroform, and a preferred example is dichloromethane.

Examples of a reagent used therein include an aqueous hydrogen peroxide solution, peracetic acid, pertrifluoroacetic acid, dimethyldioxirane, Oxone (trade name) and m-chloroperbenzoic acid, and a preferred example is m-chloroperbenzoic acid.

The reaction temperature is −30° C. to 50° C., and preferably −10° C. to 30° C. The reaction time is 5 minutes to 24 hours, and preferably 10 minutes to 12 hours.

When a workup is needed, the workup may be carried out according to the following procedure, for example. The precipitate is filtered, and then the filtrate is diluted with ethyl acetate. Subsequently, sodium sulfite is added to the dilution, and the mixture is washed sequentially with a 1 N aqueous solution of sodium hydroxide and saturated brine. Subsequently, the mixture is dried over a desiccant such as sodium sulfate, and the solvent is distilled off under reduced pressure. The resulting residue is purified by silica gel chromatography.

The compound of the present invention can be produced by using the methods described above, and can also be easily produced from known compounds according to Reference Examples and Examples that will be described below.

The compound of the present invention represented by the general formula (I) or a pharmaceutically acceptable salt thereof obtained by the methods described above has an excellent hypoglycemic action, and can therefore be used as an active ingredient of a pharmaceutical composition that can be used in the treatment and/or prevention of type 1 diabetes, type 2 diabetes, gestational diabetes, hyperglycemia due to other factors, impaired glucose tolerance (IGT), obesity, diabetes-associated diseases (for example, hyperlipidemia, hypercholesterolemia, abnormal lipid metabolism, hypertension, fatty liver, metabolic syndrome, edema, heart failure, angina pectoris, myocardial infarction, arteriosclerosis, hyperuricemia, and gout), or diabetic complications (for example, retinosis, kidney failure, neuropathy, cataract, gangrenous leg, infections, and ketosis).

Furthermore, since the compound of the present invention or a pharmaceutically acceptable salt thereof has an excellent β cell- or pancreas-protecting action, the compound or the salt can be used as an active ingredient of a pharmaceutical composition that can be used to protect β cells or the pancreas.

The compound of the present invention can also be used in combination with a therapeutic drug for diabetes other than the compound of the present invention, a therapeutic drug for diabetic complications, a therapeutic drug for hyperlipidemia, a therapeutic drug for hypertension, and the like.

When a pharmaceutical composition containing the compound of the present invention represented by the general formula (I) or a pharmaceutically acceptable salt thereof is administered to a mammal (for example, a human being, a horse, a cow or a pig; preferably a human being), the pharmaceutical composition can be administered systemically or topically, and orally or parenterally.

The pharmaceutical composition of the present invention can be prepared according to the formulation methods for various conventionally used preparations, by selecting appropriate dosage forms in accordance with the administration mode.

Examples of dosage forms of the pharmaceutical composition for oral use include tablets, pills, powders, granules, capsules, liquids, suspensions, emulsions, syrups, and elixirs. Pharmaceutical compositions of such dosage forms can be prepared according to conventional methods, by appropriately selecting as necessary, excipients, binders, disintegrants, lubricating agents, swelling agents, swelling aids, coating agents, plasticizers, stabilizers, antiseptics, antioxidants, colorants, dissolution aids, suspending agents, emulsifiers, sweeteners, preservatives, buffers, diluents, wetting agents and the like, which are conventionally used as additives.

Examples of dosage forms of a pharmaceutical composition for parenteral use include injectable preparations, ointments, gels, creams, poultices, patches, aerosols, inhalants, sprays, eye drops, nose drops, and suppositories. Pharmaceutical compositions of such dosage forms can be prepared according to conventional methods, by appropriately selecting as necessary, stabilizers, antiseptics, dissolution aids, moisturizers, preservatives, antioxidants, fragrances, gelling agents, neutralizing agents, buffers, isotonic agents, surfactants, colorants, buffering agents, thickeners, wetting agents, fillers, absorption promoting agents, suspending agents, binders, and the like, which are conventionally used as additives.

The amount of administration of the compound of the present invention represented by the general formula (I) or a pharmaceutically acceptable salt thereof may vary according to symptoms, age, body weight or the like. However, in the case of oral administration, the compound or the salt is administered once or several times a day, in an amount of 1 to 2000 mg, and preferably 1 to 400 mg, in terms of the compound, per dose for an adult; and in the case of parenteral administration, the compound or the salt is administered once or several times a day, in an amount of 0.01 to 500 mg, and preferably 0.1 to 300 mg, in terms of the compound, per dose for an adult.

Hereinafter, the present invention will be described in more detail by way of Reference Examples, Examples, Formulation Examples and Test Examples, but the scope of the present invention is not intended to be limited to these.

EXAMPLES

Reference Example 1

3-Fluoro-4-methylthiobenzonitrile

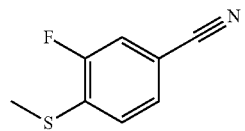

Sodium thiomethoxide (3.88 g, 55.3 mmol) was added to a dimethylformamide (100 mL) solution of 3,4-difluorobenzonitrile (7.00 g, 50.3 mmol) over 20 minutes under ice water cooling, and the mixture was further stirred for 20 minutes at the same temperature. Water (200 mL) was added to the reaction mixture, and the solid precipitated therefrom was collected by filtration and washed with water. Thus, a crude product of the title compound was obtained. The crude product thus obtained was dissolved in ethyl acetate, and was dried over anhydrous sodium sulfate. The solvent was distilled off under reduced pressure. Thus, the title compound (7.30 g, yield: 87%) was obtained.

$^1$H-NMR (400 MHz, CDCl$_3$) δppm: 7.42 (1H, dd, J=8 Hz, 1 Hz), 7.28 (1H, dd, J=10 Hz, 1 Hz), 7.24 (1H, dd, J=10 Hz, 8 Hz), 2.52 (3H, s).

Reference Example 2

3-Fluoro-4-methylsulfonylbenzonitrile

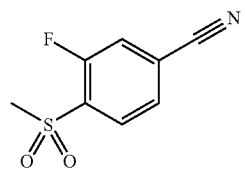

3-Chloroperbenzoic acid (24.3 g, 91.7 mmol) was added to a methylene chloride (220 mL) solution of the compound obtained in Reference Example 1 (7.30 g, 43.7 mmol) under ice water cooling, and the mixture was stirred for 30 minutes at the same temperature and then was further stirred for 19 hours at room temperature. A saturated aqueous solution of sodium hydrogen carbonate was added to the reaction mixture, and the mixture was subjected to extraction two times with methylene chloride. The organic layer thus obtained was washed with a 1.5M aqueous solution of sodium sulfite, and then was dried over anhydrous sodium sulfate. The solvent was distilled off under reduced pressure. The resulting residue was washed with hexane-ethyl acetate (5:1, v/v). Thus, the title compound (8.27 g, yield: 95%) was obtained.

$^1$H-NMR (400 MHz, CDCl$_3$) δppm: 8.12 (1H, dd, J=9 Hz, 8 Hz), 7.67 (1H, dd, J=8 Hz, 1 Hz), 7.58 (1H, dd, J=9 Hz, 1 Hz), 3.27 (3H, s).

Reference Example 3

3-Fluoro-N'-hydroxy-4-(methylsulfonyl)benzenecarboxylmidamide

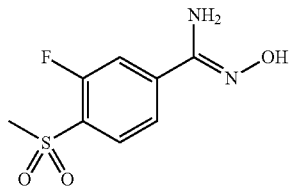

A 50% aqueous solution of hydroxylamine (6.25 mL, 94.6 mmol) was added to an ethanol (63.0 mL) solution of the compound obtained in Reference Example 2 (6.28 g, 31.5 mmol) at room temperature, and then the mixture was stirred for 30 minutes at the same temperature and then was further stirred for 30 minutes under ice water cooling. The solid precipitated therefrom was collected by filtration, and was washed with 2-propanol-water (10:1, v/v). Thus, the title compound (6.45 g, yield: 88%) was obtained.

$^1$H-NMR (400 MHz, DMSO-d$_6$) δppm: 10.14 (1H, s), 7.85 (1H, t, J=12 Hz, 8 Hz), 7.77 (1H, dd, J=8 Hz, 1 Hz), 7.74 (1H, dd, J=12 Hz, 1 Hz), 6.07 (2H, s), 3.34 (3H, s).

Reference Example 4

Ethyl 2-(4-cyanophenoxy)butanoate

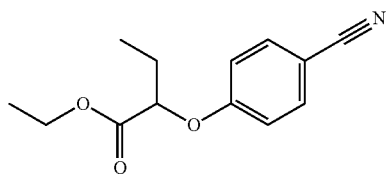 [SMILES: CCOC(=O)C(CC)Oc1ccc(C#N)cc1]

Potassium carbonate (14.5 g, 105 mmol) was added to an acetonitrile (80.0 mL) solution of 4-cyanophenol (5.00 g, 42.0 mmol) and ethyl 2-bromobutyrate (9.83 g, 50.4 mmol) at room temperature, and the mixture was stirred for 3 hours at 80° C. After the mixture was cooled to room temperature, water was added to the reaction mixture, and the mixture was subjected to extraction two times with ethyl acetate. The organic layer thus obtained was washed with saturated brine, and then was dried over anhydrous sodium sulfate. The solvent was distilled off under reduced pressure, and the resulting residue was purified by silica gel column chromatography (hexane:ethyl acetate=9:1→2:1, v/v). Thus, the title compound (9.79 g, yield: 100%) was obtained.

$^1$H-NMR (400 MHz, CDCl$_3$) δppm: 7.58 (2H, d, J=9 Hz), 6.92 (2H, d, J=9 Hz), 4.61 (1H, t, J=6 Hz), 4.25-4.20 (2H, m), 2.06-1.99 (2H, m), 1.25 (3H, t, J=7 Hz), 1.08 (3H, t, J=7 Hz).

Reference Example 5

Ethyl 2-{4-[amino(hydroxyimino)methyl]phenoxy}butanoate

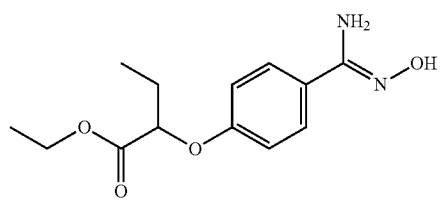 [SMILES: CCOC(=O)C(CC)Oc1ccc(/C(N)=N/O)cc1]

A 50% aqueous solution of hydroxylamine (8.32 mL, 126 mmol) was added to an ethanol (42.0 mL) solution of the compound obtained in Reference Example 4 (9.97 g, 42.0 mmol) at room temperature, and the mixture was stirred for 2.5 hours at 80° C. After the reaction mixture was cooled to room temperature, water was added to the reaction mixture, and the mixture was subjected to extraction two times with ethyl acetate. The organic layer thus obtained was washed with saturated brine, and then was dried over anhydrous sodium sulfate. The solvent was distilled off under reduced pressure, and the resulting residue was purified by silica gel column chromatography (hexane:ethyl acetate=1:1→0:1, v/v). Thus, the title compound (9.82 g, yield: 88%) was obtained.

$^1$H-NMR (400 MHz, CDCl$_3$) δppm: 7.54 (2H, d, J=9 Hz), 6.89 (2H, d, J=9 Hz), 4.81 (2H, s), 4.58 (1H, t, J=6 Hz), 4.22 (2H, q, J=7 Hz), 2.03-1.97 (2H, m), 1.24 (3H, t, J=7 Hz), 1.08 (3H, t, J=8 Hz).

Reference Example 6

Ethyl 2-[4-(5-isopropyl-1,2,4-oxadiazol-3-yl)phenoxy]butanoate

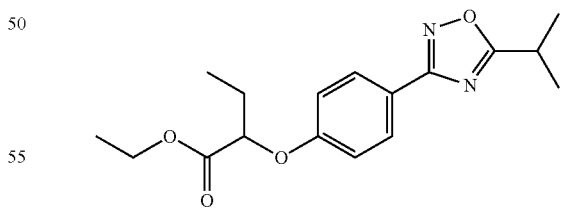

Isobutyric acid chloride (1.29 mL, 12.4 mmol) was added to a pyridine (16.0 mL) solution of the compound obtained in Reference Example 5 (3.00 g, 11.3 mmol) at room temperature, and the mixture was stirred for 2 hours at 100° C. After the mixture was cooled to room temperature, the reaction mixture was concentrated under reduced pressure, and water was added thereto. The mixture was subjected to extraction two times with ethyl acetate, and the organic layer thus obtained was washed with a 1 M aqueous hydrochloric acid solution and saturated brine and was dried over anhydrous sodium sulfate. The solvent was distilled off under reduced pressure, and the resulting residue was purified by silica gel column chromatography (hexane:ethyl acetate=3:1, v/v). Thus, the title compound (3.25 g, yield: 91%) was obtained.

$^1$H-NMR (400 MHz, CDCl$_3$) δppm: 8.00 (2H, d, J=9 Hz), 6.95 (2H, d, J=9 Hz), 4.62 (1H, t, J=6 Hz), 4.22 (2H, q, J=7 Hz), 3.31-3.22 (1H, m), 2.05-1.99 (2H, m), 1.45 (6H, d, J=7 Hz), 1.24 (3H, t, J=7 Hz), 1.10 (3H, t, J=7 Hz).

Reference Example 7

2-[4-(5-Isopropyl-1,2,4-oxadiazol-3-yl)phenoxy]butanoic acid

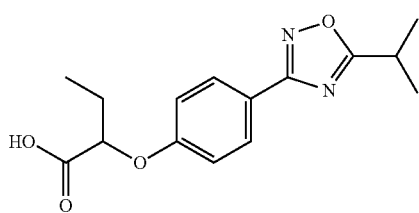 [SMILES: CCC(Oc1ccc(-c2noc(C(C)C)n2)cc1)C(=O)O]

The compound obtained in Reference Example 6 (1.50 g, 4.71 mmol) was dissolved in a tetrahydrofuran (6.00 mL)-methanol (6.00 mL) solution, and a 1 M aqueous solution of sodium hydroxide (5.65 mL, 5.65 mmol) was added thereto. The mixture was stirred for 30 minutes at room temperature. The reaction mixture was concentrated under reduced pressure, and water and a 1 M aqueous hydrochloric acid solution were added thereto. The mixture was subjected to extraction two times with ethyl acetate, and the organic layer thus obtained was washed with saturated brine and then was dried over anhydrous sodium sulfate. The solvent was distilled off under reduced pressure, and the resulting residue was washed with hexane. Thus, the title compound (1.30 g, yield: 95%) was obtained.

$^1$H-NMR (400 MHz, CDCl$_3$) δppm: 8.00 (2H, d, J=9 Hz), 6.98 (2H, d, J=9 Hz), 4.69 (1H, dd, J=6 Hz, 5 Hz), 3.31-3.25 (1H, m), 2.10-2.03 (2H, m), 1.45 (6H, d, J=7 Hz), 1.13 (3H, t, J=7 Hz).

Reference Example 8

N',4-dihydroxybenzenecarboxyimidamide

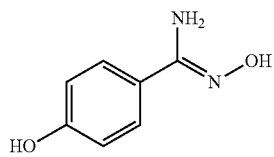

A 50% aqueous solution of hydroxylamine (39.6 mL, 400 mmol) was added to a 2-propanol (400 mL) solution of 4-cyanophenol (23.8 g, 200 mmol) at room temperature, and the mixture was stirred for 4 hours at 80° C. and then was cooled to room temperature. A solid precipitated therefrom was collected by filtration, and was washed with 2-propanol-water (10:1, v/v). Thus, the title compound 26.2 g, yield: 86%) was obtained.

$^1$H-NMR (400 MHz, DMSO-d$_6$) δppm: 9.40-9.36 (1H, br-s), 7.47 (2H, d, J=9 Hz), 6.72 (2H, d, J=9 Hz), 5.61 (2H, s).

Reference Example 9

4-(5-Isopropyl-1,2,4-oxadiazol-3-yl)phenol

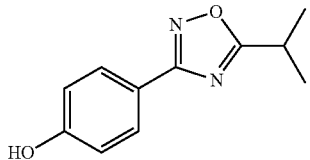

The synthesis was carried out in the same manner as in Reference Example 6, except that the compound obtained in Reference Example 8 (20.0 g, 131 mmol) was used in place of ethyl 2-{4-[amino(hydroxyimino)methyl]phenoxy}butanoate. Thus, the title compound (19.2 g, yield: 72%) was obtained.

$^1$H-NMR (400 MHz, CDCl$_3$) δppm: 7.96 (2H, d, J=9 Hz), 6.91 (2H, d, J=9 Hz), 5.73-5.69 (1H, br-s), 3.30-3.25 (1H, m), 1.45 (7H, d, J=7 Hz).

Reference Example 10

Ethyl 2-[4-(5-isopropyl-1,2,4-oxadiazol-3-yl)phenoxy]propionate

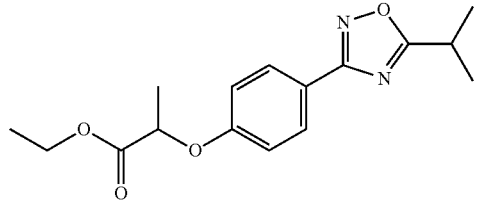 [SMILES: CCOC(=O)C(C)Oc1ccc(-c2noc(C(C)C)n2)cc1]

The synthesis was carried out in the same manner as in Reference Example 4, except that the compound obtained in Reference Example 9 (2.00 g, 9.79 mmol) was used in place of 4-cyanophenol, and ethyl 2-bromopropionate (2.13 g, 11.8 mmol) was used in place of ethyl 2-bromobutyrate. Thus, the title compound (2.64 g, yield: 89%) was obtained.

$^1$H-NMR (400 MHz, CDCl$_3$) δppm: 8.00 (2H, d, J=9 Hz), 6.95 (2H, d, J=9 Hz), 4.81 (1H, q, J=6 Hz), 4.22 (2H, q, J=7 Hz), 3.29-3.23 (1H, m), 1.65 (3H, d, J=6 Hz), 1.44 (6H, d, J=7 Hz), 1.25 (3H, t, J=7 Hz).

Reference Example 11

2-[4-(5-Isopropyl-1,2,4-oxadiazol-3-yl)phenoxy]propionic acid

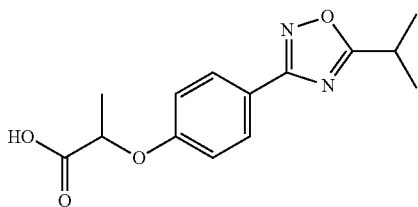 [SMILES: CC(Oc1ccc(-c2noc(C(C)C)n2)cc1)C(=O)O]

The synthesis was carried out in the same manner as in Reference Example 7, except that the compound obtained in Reference Example 10 was used in place of ethyl 2-[4-(5-isopropyl-1,2,4-oxadiazol-3-yl)phenoxy]butanoate. Thus, the title compound (1.26 g, yield: 87%) was obtained.

$^1$H-NMR (400 MHz, CDCl$_3$) δppm: 8.01 (2H, d, J=9 Hz), 6.98 (2H, d, J=9 Hz), 4.88 (1H, q, J=7 Hz), 3.32-3.25 (1H, m), 1.70 (3H, d, J=7 Hz), 1.45 (6H, d, J=7 Hz).

Reference Example 12

Ethyl 2-[4-(5-isopropyl-1,2,4-oxadiazol-3-yl)phenoxy]pentanoate

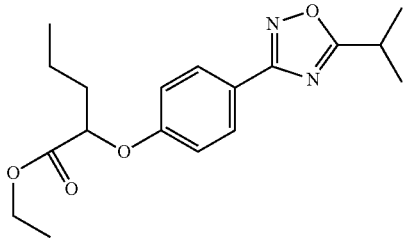 [SMILES: CCCC(Oc1ccc(-c2noc(C(C)C)n2)cc1)C(=O)OCC]

The synthesis was carried out in the same manner as in Reference Example 10, except that ethyl 2-bromopentanoate (302 (L, 1.76 mmol) was used in place of ethyl 2-bromopropionate. Thus, the title compound (488 mg, yield: 100%) was obtained.

1H-NMR (400 MHz, CDCl$_3$) (ppm: 8.00 (2H, d, J=9 Hz), 6.95 (2H, d, J=9 Hz), 4.68 (1H, dd, J=8 Hz, 5 Hz), 4.22 (2H, q, J=7 Hz), 3.26 (1H, sept, J=7 Hz), 2.02-1.89 (2H, m), 1.62-1.51 (2H, m), 1.45 (6H, d, J=7 Hz), 1.24 (3H, t, J=7 Hz), 0.99 (3H, t, J=7 Hz).

Reference Example 13

2-[4-(5-Isopropyl-1,2,4-oxadiazol-3-yl)phenoxy]pentanoic acid

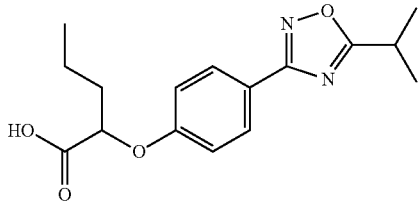 [SMILES: CCCC(Oc1ccc(-c2noc(C(C)C)n2)cc1)C(=O)O]

The synthesis was carried out in the same manner as in Reference Example 7, except that the compound obtained in Reference Example 12 (590 mg, 1.78 mmol) was used in place of ethyl 2-[4-(5-isopropyl-1,2,4-oxadiazol-3-yl)phenoxy]butanoate. Thus, the title compound (419 mg, yield: 78%) was obtained.

1H-NMR (400 MHz, CDCl$_3$) (ppm: 8.00 (2H, d, J=9 Hz), 6.97 (2H, d, J=9 Hz), 4.73 (1H, dd, J=8 Hz, 5 Hz), 3.28 (1H, sept, J=7 Hz), 2.05-1.97 (2H, m), 1.85-1.54 (2H, m), 1.45 (6H, d, J=7 Hz), 1.00 (3H, t, J=7 Hz).

Reference Example 14

Ethyl 2-[4-(5-ethyl-1,2,4-oxadiazol-3-yl)phenoxy]butanoate

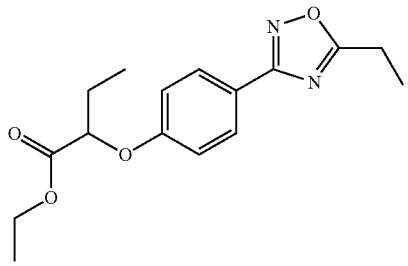 [SMILES: CCOC(=O)C(CC)Oc1ccc(-c2noc(CC)n2)cc1]

The synthesis was carried out in the same manner as in Reference Example 6, except that the compound obtained in Reference Example 5 (4.10 g, 15.4 mmol) was used, and propionic acid chloride (1.47 mL, 17.0 mmol) was used in place of isobutyric acid chloride. Thus, the title compound (1.95 g, yield: 42%) was obtained.

$^1$H-NMR (400 MHz, CDCl$_3$) δppm: 8.00 (2H, d, J=8 Hz), 6.96 (2H, d, J=8 Hz), 4.63 (1H, t, J=6 Hz), 4.23 (2H, q, J=7 Hz), 2.96 (2H, q, J=7 Hz), 2.02 (2H, q, J=7 Hz), 1.44 (3H, t, J=7 Hz), 1.25 (3H, t, J=7 Hz), 1.10 (3H, t, J=7 Hz).

Reference Example 15

2-[4-(5-Ethyl-1,2,4-oxadiazol-3-yl)phenoxy]butanoic acid

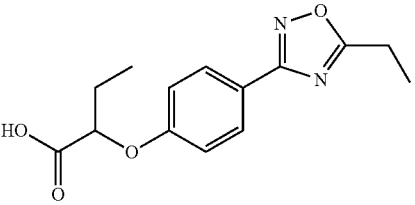 [SMILES: CCc1nc(-c2ccc(OC(CC)C(=O)O)cc2)no1]

The synthesis was carried out in the same manner as in Reference Example 7, except that the compound obtained in Reference Example 14 (1.95 g, 6.41 mmol) was used in place of ethyl 2-[4-(5-isopropyl-1,2,4-oxadiazol-3-yl)phenoxy]butanoate. Thus, the title compound (1.77 g, yield: 100%) was obtained.

$^1$H-NMR (400 MHz, CDCl$_3$) δppm: 8.00 (2H, d, J=9 Hz), 6.99 (2H, d, J=9 Hz), 4.69 (1H, t, J=6 Hz), 2.97 (2H, q, J=8 Hz), 2.11-2.05 (2H, m), 1.44 (3H, t, J=8 Hz), 1.13 (3H, t, J=8 Hz).

Reference Example 16

5-Hydroxypyridine-2-carbonitrile

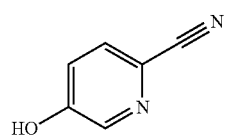

Concentrated sulfuric acid (21.0 mL) was added to a suspension of 3-amino-6-cyanopyridine (5.00 g, 42.0 mmol) in water (75.0 mL), and then a 1.6 M aqueous solution of sodium nitrite (29.0 mL, 46.4 mmol) was slowly added dropwise thereto under ice water cooling. This suspension was stirred for 6 hours at 100° C. The reaction mixture was cooled to room temperature, and then was diluted with ethyl acetate (100 mL). The organic layer was washed sequentially with water and saturated brine, and was dried over anhydrous sodium sulfate. The solvent was distilled off under reduced pressure, and the resulting residue was purified by silica gel column chromatography (hexane:ethyl acetate=9:1→1:1, v/v). Thus, the title compound was obtained.

Reference Example 17

Ethyl 2-[(6-cyanopyridin-3-yl)oxy]butanoate

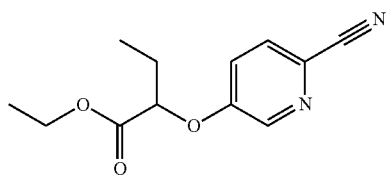 [SMILES: CCOC(=O)C(CC)Oc1ccc(C#N)nc1]

The synthesis was carried out in the same manner as in Reference Example 4, except that the compound obtained in Reference Example 16 (500 mg, 4.16 mmol) was used in place of 4-cyanophenol. Thus, the title compound was obtained.

Reference Example 18

Ethyl 2-({6-[amino(hydroxyimino)methyl]pyridin-3-yl}oxy)butanoate

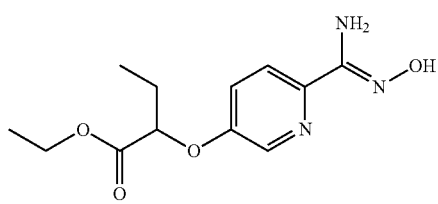 [SMILES: CCOC(=O)C(CC)Oc1ccc(/C(N)=N/O)nc1]

The synthesis was carried out in the same manner as in Reference Example 5, except that the compound obtained in Reference Example 17 (958 mg, 4.10 mmol) was used in place of ethyl 2-(4-cyanophenoxy)butanoate. Thus, the title compound was obtained.

Reference Example 19

Ethyl 2-{[6-(5-isopropyl-1,2,4-oxadiazol-3-yl)pyridin-3-yl]oxy}butanoate

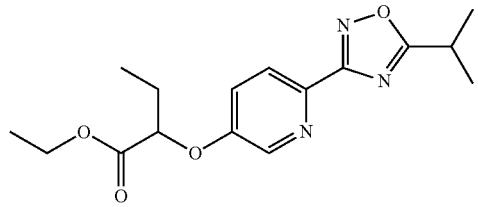 [SMILES: CCOC(=O)C(CC)Oc1ccc(-c2noc(C(C)C)n2)nc1]

The synthesis was carried out in the same manner as in Reference Example 6, except that the compound obtained in Reference Example 18 (1.10 g, 4.18 mmol) was used in place of ethyl 2-{4-[amino(hydroxyimino)methyl]phenoxy}butanoate. Thus, the title compound was obtained.

Reference Example 20

2-{[6-(5-Isopropyl-1,2,4-oxadiazol-3-yl)pyridin-3-yl]oxy}butanoic acid

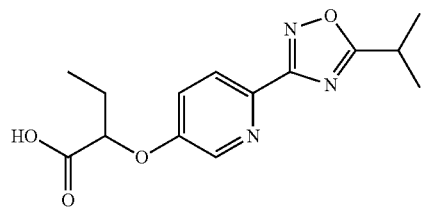 [SMILES: CCC(Oc1ccc(-c2noc(C(C)C)n2)nc1)C(=O)O]

The synthesis was carried out in the same manner as in Reference Example 6, except that the compound obtained in Reference Example 19 (1.03 g, 3.23 mmol) was used in place of ethyl 2-[4-(5-isopropyl-1,2,4-oxadiazol-3-yl)phenoxy]butanoate. Thus, the title compound was obtained.

Reference Example 21

3'-Fluoro-4'-methylthioacetophenone

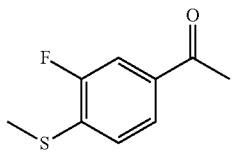

The synthesis was carried out in the same manner as in Reference Example 1, except that 3',4'-difluoroacetophenone (10.0 g, 64.0 mmol) was used in place of 3,4-difluorobenzonitrile. Thus, the title compound (10.3 g, yield: 87%) was obtained.

$^1$H-NMR (400 MHz, CDCl$_3$) δppm: 7.71 (1H, dd, J=8 Hz, 1 Hz), 7.59 (1H, dd, J=10 Hz, 1 Hz), 7.25 (1H, dd, J=10 Hz, 8 Hz), 2.57 (3H, s), 2.52 (3H, s).

Reference Example 22

({1-[3-Fluoro-4-(methylthio)phenyl]vinyl}oxy)(trimethyl)silane

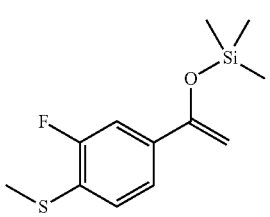

To a methylene chloride (14.0 mL) solution of the compound obtained in Reference Example 21 (500 mg, 2.71 mmol), triethylamine (605 μL, 4.34 mmol) and trimethylsilyl trifluoromethanesulfonate (688 μL, 3.80 mmol) were added at room temperature, and the mixture was stirred for 30 minutes. A saturated aqueous solution of sodium hydrogen carbonate was added to the reaction mixture, and the mixture was subjected to extraction two times with methylene chloride and was dried over anhydrous sodium sulfate. The solvent was distilled off under reduced pressure, and the product was used in the subsequent reaction.

Reference Example 23

2-Bromo-1-[3-fluoro-4-(methylthio)phenyl]ethanone

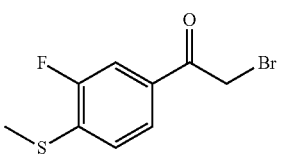

The compound obtained in Reference Example 22 was dissolved in tetrahydrofuran (14.0 mL), and N-bromosuccinimide (483 mg, 2.71 mmol) was added to the solution under ice water cooling. The mixture was stirred for 15 minutes at the same temperature. Water and saturated brine were added to the reaction mixture, and the mixture was subjected to extraction two times with ethyl acetate. The organic layer thus obtained was washed with saturated brine, and then was dried over anhydrous sodium sulfate. The solvent was distilled off under reduced pressure, and the resulting residue was purified by silica gel column chromatography (hexane:ethyl acetate=3:1→2:1, v/v). Thus, the title compound (675 mg, yield: 95%) was obtained.

$^1$H-NMR (400 MHz, CDCl$_3$) δppm: 7.75 (1H, dd, J=8 Hz, 1 Hz), 7.63 (1H, dd, J=10 Hz, 1 Hz), 7.27 (1H, dd, J=10 Hz, 8 Hz), 4.37 (2H, s), 2.54 (3H, s).

Reference Example 24

2-[3-Fluoro-4-(methylthio)phenyl]-2-oxoethyl 2-[4-(5-isopropyl-1,2,4-oxadiazol-3-yl)phenoxy]butanoate

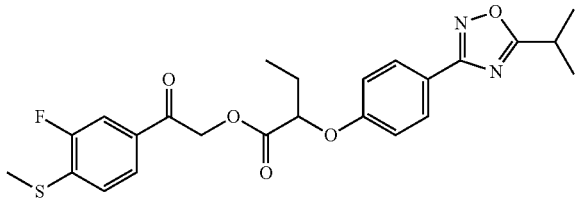 [SMILES: CCC(Oc1ccc(-c2noc(C(C)C)n2)cc1)C(=O)OCC(=O)c1ccc(SC)c(F)c1]

Triethylamine (119 μL, 0.855 mmol) was added to an acetone (2.90 mL) solution of the compound obtained in Reference Example 23 (150 mg, 0.570 mmol) and the compound obtained in Reference Example 7 (182 mg, 0.627 mmol) at room temperature, and the mixture was stirred for 30 minutes at the same temperature. Water was added to the reaction mixture, and the mixture was subjected to extraction two times with ethyl acetate. The organic layer thus obtained was washed with a saturated sodium hydrogen carbonate solution and saturated brine, and then was dried over anhydrous sodium sulfate. The solvent was distilled off under reduced pressure. Thus, the title compound (269 mg, yield: 100%) was obtained.

$^1$H-NMR (400 MHz, CDCl$_3$) δppm: 8.02 (2H, d, J=12 Hz), 7.62 (1H, dd, J=8 Hz, 1 Hz), 7.54 (1H, dd, J=10 Hz, 1 Hz), 7.24 (1H, dd, J=10 Hz, 8 Hz), 7.05 (2H, d, J=12 Hz), 5.39 (1H, d, J=16 Hz), 5.30 (1H, d, J=16 Hz), 4.81 (1H, dd, J=7 Hz, 5 Hz), 3.31-3.23 (1H, m), 2.52 (3H, s), 2.22-2.09 (2H, m), 1.45 (6H, d, J=7 Hz), 1.18 (3H, t, J=7 Hz).

Reference Example 25

3-[4-(1-{4-[3-Fluoro-4-(methylthio)phenyl]-1,3-oxazol-2-yl}propoxy)phenyl]-5-isopropyl-1,2,4-oxadiazole

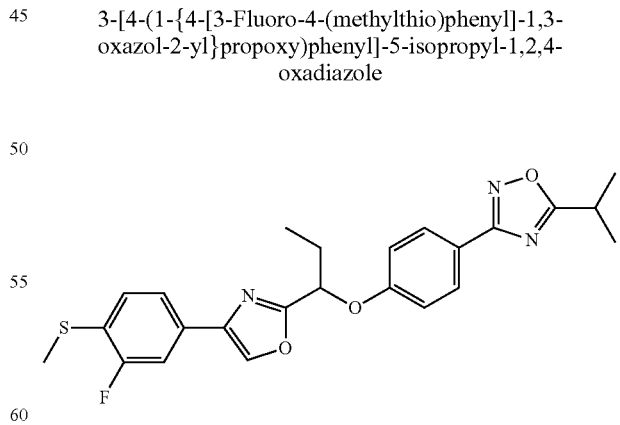

Ammonium trifluoroacetate (2.00 g) was added to the compound obtained in Reference Example 24 (164 mg, 0.346 mmol), and the mixture was stirred for 4 hours at 150° C. The reaction mixture was cooled to room temperature, subsequently water was added thereto, and the mixture was subjected to extraction two times with ethyl acetate. The organic layer thus obtained was washed with saturated brine, and then was dried over anhydrous sodium sulfate. The solvent was distilled off under reduced pressure, and the resulting residue was purified by silica gel column chromatography (hexane: ethyl acetate=1:0→2:1, v/v). Thus, the title compound (101 mg, yield: 64%) was obtained.

¹H-NMR (400 MHz, CDCl₃) δppm: 7.98 (2H, d, J=9 Hz), 7.85 (1H, s), 7.45 (1H, dd, J=8 Hz, 2 Hz), 7.42 (1H, dd, J=10 Hz, 2 Hz), 7.27 (1H, dd, J=10 Hz, 8 Hz), 7.10 (2H, d, J=9 Hz), 5.33 (1H, t, J=7 Hz), 3.29-3.20 (1H, m), 2.49 (3H, s), 2.29-2.12 (2H, m), 1.43 (6H, d, J=7 Hz), 1.08 (3H, t, J=8 Hz).

Reference Example 26

(2R)-2-[4-(5-isopropyl-1,2,4-oxadiazol-3-yl)phenoxy]butyric acid

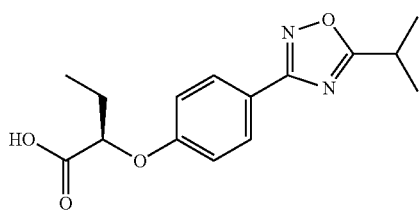 [SMILES: CC[C@@H](Oc1ccc(-c2noc(C(C)C)n2)cc1)C(=O)O]

A 60% sodium hydride (14.7 g, 367 mmol) was added to a 1,4-dioxane (300 mL) solution of the compound obtained in Reference Example 9 (30.0 g, 147 mmol) at room temperature, and the mixture was stirred for 10 minutes at the same temperature and then was heated to 100° C. Subsequently, a 1,4-dioxane (50 mL) solution of (S)-2-chlorobutyric acid (19.7 mL, 191 mmol) at 100° C. was added dropwise to the mixture, and the resulting mixture was further stirred for 4 hours at the same temperature. The reaction mixture was cooled to room temperature, and then 2 N hydrochloric acid was added thereto. The mixture was subjected to extraction two times with ethyl acetate, and the organic layer thus obtained was washed with saturated brine and then was dried over anhydrous magnesium sulfate. The solvent was distilled off under reduced pressure, and the resulting residue was washed with hexane-ethyl acetate (3:1, v/v). Thus, the title compound (30.4 g, yield: 71%) was obtained.

¹H-NMR (500 MHz, CDCl₃) δppm: 8.00 (2H, d, J=9 Hz), 6.98 (2H, d, J=9 Hz), 4.69 (1H, dd, J=7, 6 Hz), 3.32-3.24 (1H, m), 2.13-2.02 (2H, m), 1.45 (6H, d, J=7 Hz), 1.13 (3H, t, J=7 Hz).

Reference Example 27

4-(5-Ethyl-1,2,4-oxadiazol-3-yl)phenol

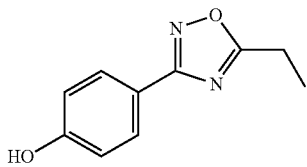

Propionic acid chloride (1.14 mL, 13.1 mmol) was added to a pyridine (20 mL) solution of the compound obtained in Reference example 8 (2.00 g, 13.1 mmol) at 0° C., and the mixture was stirred for 15 minutes at 0° C. Subsequently, the reaction mixture was heated to 80° C., and was stirred for 3 hours. The reaction mixture was cooled to room temperature, subsequently water and 2 N hydrochloric acid were added thereto, and the mixture was subjected to extraction two times with ethyl acetate. The organic layer thus obtained was washed with saturated brine, and then was dried over anhydrous sodium sulfate. The solvent was distilled off under reduced pressure, and the resulting residue was purified by silica gel column chromatography (hexane:ethyl acetate=95:5→80:20, v/v). Thus, the title compound (1.98 g, yield: 80%) was obtained.

¹H-NMR (400 MHz, CDCl₃) δppm: 7.96 (2H, d, J=9 Hz), 6.92 (2H, d, J=9 Hz), 2.97 (2H, q, J=8 Hz), 1.44 (3H, t, J=8 Hz).

Reference Example 28

(2R)-2-[4-(5-ethyl-1,2,4-oxadiazol-3-yl)phenoxy]butyric acid

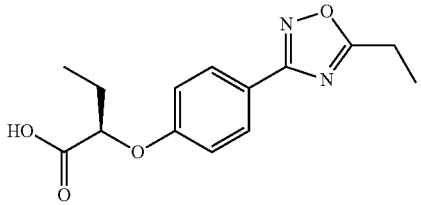 [SMILES: CCc1nc(-c2ccc(O[C@H](CC)C(=O)O)cc2)no1]

60% Sodium hydride (673 mg, 16.8 mmol) was added in small amounts to a 1,4-dioxane (28 mL) solution of the compound obtained in Reference Example 27 (800 mg, 4.21 mmol) at room temperature, and the mixture was stirred for 10 minutes at room temperature. Subsequently, a dioxane solution (2 mL) of (S)-2-chlorobutyric acid (563 uL, 5.46 mmol) was added to the reaction mixture, and the mixture was stirred for 4.5 hours at 100° C. The reaction mixture was cooled to room temperature, subsequently water and 2 N hydrochloric acid were added thereto, and the mixture was subjected to extraction three times with ethyl acetate. The organic layer thus obtained was washed with saturated brine, and then was dried over anhydrous sodium sulfate. The solvent was distilled off under reduced pressure, and the resulting residue was washed with hexane-ethyl acetate (10:1, v/v). Thus, the title compound (571 mg, yield: 66%) was obtained.

Example 1

3-[3-Fluoro-4-methylsulfonyl]phenyl]-5-{1-[4-(5-isopropyl-1,2,4-oxadiazol-3-yl)phenoxy]propyl}-1,2,4-oxadiazole

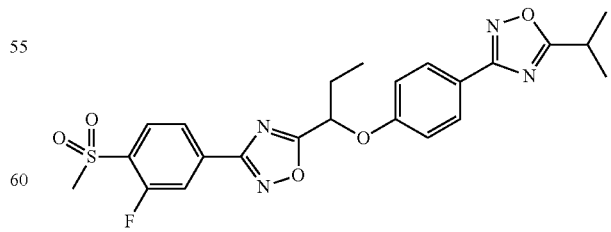

To a dimethylformamide (1.50 mL) solution of the compound obtained in Reference Example 7 (87.5 mg, 0.301 mmol), N-(3-dimethylaminopropyl)-N'-ethylcarbodiimide (116 mg, 0.603 mmol), 1-hydroxybenzotriazole monohydrate (46.2 mg, 0.301 mmol) and the compound obtained in Reference Example 3 (70.0 mg, 0.301 mmol) were added at room temperature, and the mixture was stirred for 5 hours at 100° C. The reaction mixture was cooled to room temperature, subsequently water was added to the reaction mixture, and the mixture was subjected to extraction two times with ethyl acetate. The organic layer thus obtained was washed with saturated brine, and then was dried over anhydrous sodium sulfate. The solvent was distilled off under reduced pressure, and the resulting residue was purified by silica gel column chromatography (hexane:ethyl acetate=4:1→2:3, v/v). Thus, the title compound (84 mg, yield: 57%) was obtained.

$^1$H-NMR (400 MHz, CDCl$_3$) δppm: 8.18-7.95 (5H, m), 7.17-7.03 (2H, m), 5.56 (1H, t, J=7 Hz), 3.31-3.25 (1H, m), 3.30 (3H, s), 2.47-2.16 (2H, m), 1.45 (6H, d, J=7 Hz), 1.16 (3H, t, J=7 Hz); MS (FAB$^+$) m/z: 487 [M+H]$^+$ Example 2

3-[3-Fluoro-4-methylsulfonyl]phenyl]-5-{1-[4-(5-isopropyl-1,2,4-oxadiazol-3-yl)phenoxy]ethyl}-1,2,4-oxadiazole

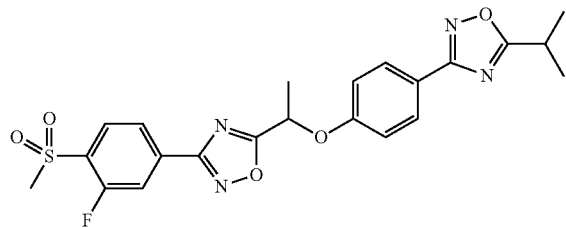 [SMILES: CC(C)c1nc(-c2ccc(OC(C)c3nc(-c4ccc(S(C)(=O)=O)c(F)c4)no3)cc2)no1]

The synthesis was carried out in the same manner as in Example 1, except that the compound obtained in Reference Example 11 (59.5 mg, 0.215 mmol) was used in place of 2-[4-(5-isopropyl-1,2,4-oxadiazol-3-yl)phenoxy]butanoic acid. Thus, the title compound (96 mg, yield: 94%) was obtained.

$^1$H-NMR (400 MHz, CDCl$_3$) δppm: 8.18-7.95 (5H, m), 7.17-7.03 (2H, m), 5.77 (1H, q, J=7 Hz), 3.31-3.26 (1H, m), 3.30 (3H, s), 1.95 (3H, d, J=7 Hz), 1.45 (6H, d, J=7 Hz); MS (FAB$^+$) m/z: 473 [M+H]$^+$ Example 3

3-[3-Fluoro-4-(methylsulfonyl)phenyl]-5-{1-[4-(5-isopropyl-1,2,4-oxadiazol-3-yl)phenoxy]butyl}-1,2,4-oxadiazole

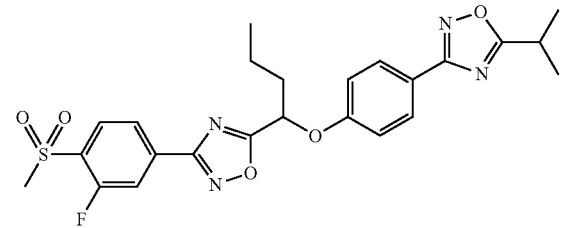 [SMILES: CCCC(Oc1ccc(-c2noc(C(C)C)n2)cc1)c1nc(-c2ccc(S(C)(=O)=O)c(F)c2)no1]

The synthesis was carried out in the same manner as in Example 1, except that the compound obtained in Reference Example 13 (210 mg, 1.38 mmol) was used in place of 2-[4-(5-isopropyl-1,2,4-oxadiazol-3-yl)phenoxy]butanoic acid. Thus, the title compound (240 mg, yield: 53%) was obtained.

$^1$H-NMR (400 MHz, CDCl$_3$) δppm: 8.18-7.95 (5H, m), 7.17-7.03 (2H, m), 5.56 (1H, t, J=7 Hz), 3.31-3.25 (1H, m), 3.30 (3H, s), 2.47-2.16 (2H, m), 1.75-1.46 (2H, m), 1.45 (6H, d, J=7 Hz), 1.25 (3H, t, J=7 Hz); MS (ESI) m/z: 501 [M+H]$^+$.

Example 4

5-Ethyl-3-[4-(1-{3-[3-fluoro-4-(methylsulfonyl)phenyl]-1,2,4-oxadiazol-5-yl}propoxy)phenyl]-1,2,4-oxadiazole

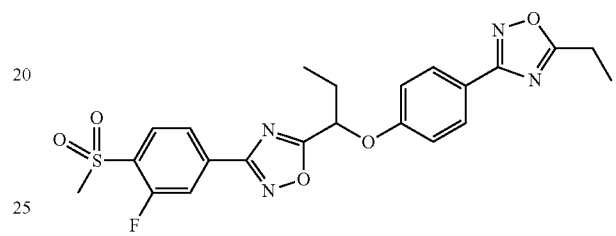

The synthesis was carried out in the same manner as in Example 1, except that the compound synthesized in Reference Example 15 (112 mg, 0.431 mmol) was used in place of 2-[4-(5-isopropyl-1,2,4-oxadiazol-3-yl)phenoxy]butanoic acid. Thus, the title compound (129 mg, yield: 63%) was obtained.

$^1$H-NMR (400 MHz, DMSO-d$_6$) δppm: 8.11-8.03 (2H, m), 7.98-7.92 (2H, m), 7.28-7.23 (2H, m), 6.08 (1H, t, J=7 Hz), 3.37 (3H, s), 3.01 (2H, q, J=7 Hz), 2.51-2.49 (1H, m), 2.24-2.18 (2H, m), 1.32 (3H, t, J=7 Hz), 1.06 (3H, t, J=7 Hz); MS (FAB$^+$) m/z: 473 [M+H]$^+$.

Example 5

5-(1-{3-[3-Fluoro-4-(methylsulfonyl)phenyl]-1,2,4-oxadiazol-5-yl}propoxy)-2-(5-isopropyl-1,2,4-oxadiazol-3-yl)pyridine

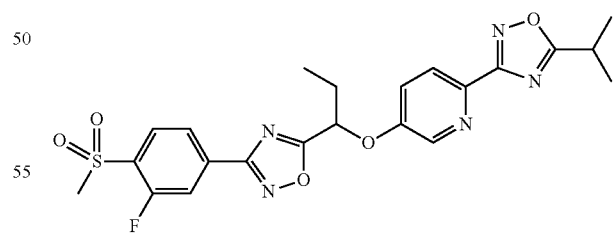

The synthesis was carried out in the same manner as in Example 1, except that the compound synthesized in Reference Example 20 (300 mg, 1.03 mmol) was used in place of 2-[4-(5-isopropyl-1,2,4-oxadiazol-3-yl)phenoxy]butanoic acid. Thus, the title compound (189 mg, yield: 63%) was obtained.

$^1$H-NMR (400 MHz, DMSO-d$_6$) δppm: 8.60 (1H, d, J=3 Hz), 8.08-8.02 (4H, m), 7.74 (1H, dd, J=9 Hz, 3 Hz), 6.16

(1H, t, J=6 Hz), 3.39 (3H, s), 3.37-3.30 (1H, m), 2.29-2.21 (2H, m), 1.37 (6H, d, J=6 Hz), 1.08 (3H, t, J=7 Hz); MS (FAB⁺) m/z: 488 [M+H]⁺.

Example 6

3-[4-(1-{4-[3-Fluoro-4-(methylsulfonyl)phenyl]-1,3-oxazol-2-yl}propoxy)phenyl]-5-isopropyl-1,2,4-oxadiazole

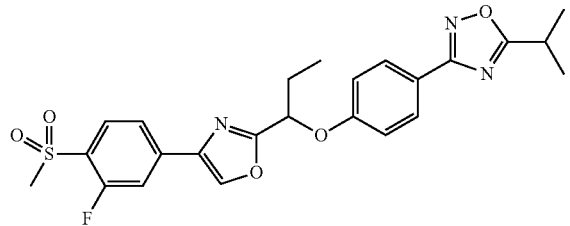

3-Chloroperbenzoic acid (113 mg, 0.425 mmol) was added to a methylene chloride (2.20 mL) solution of the compound obtained in Reference Example 25 (97.2 g, 0.213 mmol) under ice water cooling, and the mixture was stirred for 15 minutes and then was further stirred for 13 hours at room temperature. A saturated aqueous solution of sodium hydrogen carbonate was added to the reaction mixture, and the mixture was subjected to extraction two times with methylene chloride. The organic layer thus obtained was washed with a 1.5 M aqueous solution of sodium sulfite, and then was dried over anhydrous sodium sulfate. The solvent was distilled off under reduced pressure, and the resulting residue was purified by silica gel column chromatography (hexane:ethyl acetate=4:1→1:1, v/v). Thus, the title compound (101 mg, yield: 64%) was obtained.

¹H-NMR (400 MHz, CDCl₃) δppm: 8.04-7.98 (4H, m), 7.70-7.67 (2H, m), 7.14-7.10 (2H, m), 5.38 (1H, t, J=7 Hz), 3.32-3.23 (1H, m), 3.26 (3H, s), 2.60-2.11 (2H, m), 1.46 (6H, d, J=7 Hz), 1.12 (3H, t, J=7 Hz); MS (FAB⁺) m/z: 486 [M+H]⁺.

Compounds of Examples 7 to 21 were obtained by making reference to the Reference Examples and Examples described above.

TABLE 1

| Example | Structural formula | NMR data |
|---|---|---|
| 7 | | ¹H-NMR (400 MHz, DMSO-d₆) δ ppm: 8.26 (2H, d, J = 9 Hz), 8.12 (2H, d, J = 9 Hz), 7.95 (2H, d, J = 9 Hz), 7.25 (2H, d, J = 9 Hz), 6.03 (1H, t, J = 7 Hz), 3.29 (3H, s), 2.98 (2H, q, J = 7 Hz), 2.25-2.18 (2H, m), 1.32 (3H, t, J = 7 Hz), 1.06 (3H, t, J = 7 Hz); MS (FAB⁺) m/z: 455 [M + H]⁺. |
| 8 | | ¹H-NMR (400 MHz, DMSO-d₆) δ ppm: 8.26-8.20 (2H, m), 8.13-8.07 (2H, m), 7.98-7.89 (2H, m), 7.25-7.14 (2H, m), 6.00 (1H, t, J = 7 Hz), 3.33-3.29 (4H, m), 2.33-2.12 (2H, m), 1.32 (6H, d, J = 7 Hz), 1.06 (3H, t, J = 7 Hz); MS (FAB⁺) m/z: 469 [M + H]⁺. |
| 9 | | ¹H-NMR (400 MHz, DMSO-d₆) δ ppm: 8.26-7.80 (5H, m), 7.25-7.14 (2H, m), 6.00 (1H, t, J = 7 Hz), 3.33-3.29 (4H, m), 2.23-2.12 (2H, m), 1.32 (6H, d, J = 7 Hz), 1.06 (3H, t, J = 7 Hz); MS (FAB⁺) m/z: 487 [M + H]⁺. |
| 10 | | ¹H-NMR (400 MHz, DMSO-d₆) δ ppm: 8.26-8.20 (2H, m), 8.13-8.07 (2H, m), 7.98-7.89 (2H, m), 7.25-7.14 (2H, m), 6.00 (1H, t, J = 7 Hz), 3.31 (3H, s), 2.33-2.12 (2H, m), 1.32 (9H, s), 1.06 (3H, t, J = 7 Hz); MS (FAB⁺) m/z: 483 [M + H]⁺. |

TABLE 1-continued

| Example | Structural formula | NMR data |
|---|---|---|
| 11 | | ¹H-NMR (400 MHz, CDCl₃) δ ppm: 9.42 (1H, d, J = 2 Hz), 8.65 (1H, dd, J = 8 Hz, 2 Hz), 8.13 (1H, d, J = 8 Hz), 8.09-8.01 (2H, m), 7.13-7.08 (2H, m), 5.56 (1H, t, J = 7 Hz), 3.31 (3H, s), 3.30-3.28 (1H, m), 2.41-2.23 (2H, m), 1.46 (6H, d, J = 7 Hz), 1.18 (3H, t, J = 7 Hz); MS (FAB⁺) m/z: 470 [M + H]⁺. |
| 12 | | ¹H-NMR (400 MHz, CDCl₃) δ ppm: 8.20-8.00 (5H, m), 7.12-7.02 (2H, m), 5.54 (1H, t, J = 7 Hz), 3.30-3.28 (1H, m), 3.13 (3H, s), 2.81 (3H, s), 2.37-2.24 (2H, m), 1.46 (6H, d, J = 7 Hz), 1.17 (3H, t, J = 7 Hz); MS (FAB⁺) m/z: 483 [M + H]⁺. |

TABLE 2

| Example | Structural formula | NMR data |
|---|---|---|
| 13 | | ¹H-NMR (400 MHz, CDCl₃) δ ppm: 8.25 (1H, d, J = 8 Hz), 8.05-7.89 (4H, m), 7.11-7.10 (2H, m), 5.56 (1H, t, J = 7 Hz), 3.32-3.26 (1H, m), 3.24 (3H, s), 2.73 (3H, s), 2.38-2.26 (2H, m), 1.46 (6H, d, J = 7 Hz), 1.19 (3H, t, J = 7 Hz); MS (FAB⁺) m/z: 483 [M + H]⁺. |
| 14 | | ¹H-NMR (400 MHz, CDCl₃) δ ppm: 9.33 (1H, d, J = 2 Hz), 8.38-8.26 (2H, m), 8.10-8.15 (2H, m), 7.12-7.06 (2H, m), 4.92 (1H, t, J = 7 Hz), 3.35-3.25 (1H, m), 3.31 (3H, s), 2.21-2.13 (2H, m), 1.46 (6H, d, J = 7 Hz), 1.22 (3H, t, J = 7 Hz); MS (FAB⁺) m/z: 470 [M + H]⁺. |
| 15 | | ¹H-NMR (400 MHz, DMSO-d₆) δ ppm: 8.62 (1H, s), 8.07-7.96 (4H, m), 6.61-6.60 (1H, m), 6.08-6.04 (1H, m), 3.34-3.24 (4H, m), 2.51-2.48 (2H, m), 1.34 (6H, d, J = 7 Hz), 0.95 (3H, d, J = 7 Hz); MS (FAB⁺) m/z: 488 [M + H]⁺. |
| 16 | | ¹H-NMR (400 MHz, CDCl₃) δ ppm: 8.09-7.88 (5H, m), 6.84-6.80 (2H, m), 3.28-3.26 (4H, m), 1.95 (6H, s), 1.32 (6H, d, J = 7 Hz); MS (FAB⁺) m/z: 488 [M + H]⁺. |

TABLE 2-continued

| Example | Structural formula | NMR data |
|---|---|---|
| 17 | | $^1$H-NMR (400 MHz, CDCl$_3$) δ ppm: 8.09-7.90 (5H, m), 7.04-7.00 (2H, m), 5.28 (1H, d, J = 7 Hz), 3.29-3.18 (4H, m), 2.60-2.46 (1H, m), 1.41 (6H, d, J = 7 Hz), 1.19 (3H, d, J = 7 Hz), 1.04 (3H, d, J = 7 Hz); MS (FAB$^+$) m/z: 502 [M + H]$^+$. |
| 18 | | $^1$H-NMR (400 MHz, DMSO-d$_6$) δ ppm: 8.14-7.95 (5H, m), 7.31-7.25 (2H, m), 6.06 (1H, t, J = 7 Hz), 3.42 (3H, s), 2.66 (3H, s), 2.54-2.52 (2H, m), 1.09 (3H, t, J = 7 Hz); MS (FAB$^+$) m/z: 459 [M + H]$^+$. |

TABLE 3

| Example | Structural formula | NMR data |
|---|---|---|
| 19 | | $^1$H-NMR (400 MHz, CDCl$_3$) δ ppm: 8.10-7.94 (5H, m), 7.11-7.05 (2H, m), 5.41 (2H, s), 3.27-3.20 (4H, m), 1.42 (6H, d, J = 7 Hz); MS (FAB$^+$) m/z: 459 [M + H]$^+$. |
| 20 | | $^1$H-NMR (400 MHz, CDCl$_3$) δ ppm: 8.12-7.77 (5H, m), 6.86 (1H, d, J = 8 Hz), 5.52 (1H, t, J = 7 Hz), 3.19-3.18 (4H, m), 2.39-2.20 (5H, m), 1.42 (6H, d, J = 7 Hz), 1.26 (3H, t, J = 7 Hz). |
| 21 | | $^1$H-NMR (400 MHz, CDCl$_3$) δ ppm: 8.11-7.88 (m, 4H), 6.95-6.82 (2H, m), 5.49 (1H, t, J = 7 Hz), 3.80-3.82 (4H, m), 2.56 (3H, s), 2.31-2.15 (2H, m), 1.47 (6H, d, J = 7 Hz), 1.12 (3H, t, J = 7 Hz). |

Example 22

3-[3-Fluoro-4-(methylsulfonyl)phenyl]-5-{(1R)-1-[4-(5-isopropyl-1,2,4-oxadiazol-3-yl)phenoxy]propyl}-1,2,4-oxadiazole

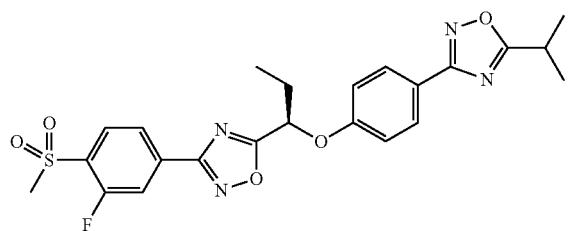 [SMILES: CC[C@@H](Oc1ccc(-c2noc(C(C)C)n2)cc1)c1nc(-c2ccc(S(C)(=O)=O)c(F)c2)no1]

To an N,N-dimethylformamide (50 mL) solution of the compound obtained in Reference Example 26 (2.90 g, 10.0 mmol), 1-hydroxybenzotriazole monohydrate (1.53 g, 10.0 mmol) and N-(3-dimethylaminopropyl)-N'-ethylcarbodiimide (3.83 g, 20.0 mmol) were added at room temperature, and the mixture was stirred for 30 minutes at the same temperature. Subsequently, the compound obtained in Reference Example 3 (2.32 g, 10.0 mmol) was added thereto at room temperature, and then the mixture was stirred for 15 minutes and then was further stirred for 3.5 hours at 100° C. The reaction mixture was cooled to room temperature, subsequently water was added thereto, and the mixture was subjected to extraction two times with ethyl acetate. The organic layer thus obtained was washed with a saturated aqueous solution of sodium hydrogen carbonate and saturated brine, and then was dried over anhydrous sodium sulfate. The solvent was distilled off under reduced pressure, and the resulting residue was purified by silica gel column chromatography (hexane:ethyl acetate=80:20→50:50, v/v). Thus, the title compound (3.99 g, yield: 82%) was obtained.

$^1$H-NMR (500 MHz, CDCl$_3$) δppm: 8.10-7.97 (5H, m), 7.06 (2H, d, J=9 Hz), 5.52 (1H, dd, J=7, 6 Hz), 3.28-3.23 (1H, m), 3.26 (3H, s), 2.35-2.20 (2H, m), 1.43 (6H, d, J=7 Hz), 1.15 (3H, t, J=7 Hz); MS (FAB$^+$) m/z: 487 [M+H]$^+$.

Example 23

5-Ethyl-3-(4-{[(1R)-1-{3-[3-fluoro-4-(methylsulfonyl)phenyl]-1,2,4-oxadiazol-5-yl}propyl]oxy}phenyl)-1,2,4-oxadiazole

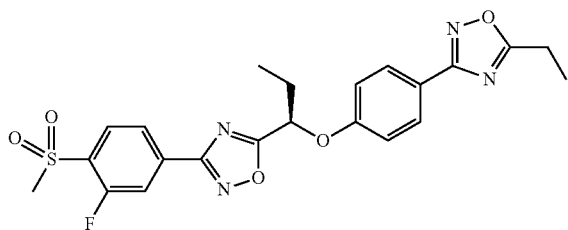 [SMILES: CCc1nc(-c2ccc(O[C@H](CC)c3nc(-c4ccc(S(C)(=O)=O)c(F)c4)no3)cc2)no1]

To a 1,3-dimethyl-2-imidazolidinone (10 mL) solution of the compound obtained in Reference Example 28 (571 mg, 2.07 mmol), 1-hydroxybenzotriazole monohydrate (317 mg, 2.07 mmol) and N-(3-dimethylaminopropyl)-N'-ethylcarbodiimide (594 mg, 3.10 mmol) were added at room temperature, and the mixture was stirred for 15 minutes at the same temperature. Subsequently, the compound obtained in Reference Example 3 (480 mg, 2.07 mmol) was added thereto, and the mixture was stirred for 30 minutes and was further stirred for 2 hours at 100° C. The reaction mixture was cooled down to room temperature, subsequently water was added to the reaction mixture, and the mixture was subjected to extraction two times with ethyl acetate. The organic layer thus obtained was washed with a saturated aqueous solution of sodium hydrogen carbonate and 10% brine, and then was dried over anhydrous sodium sulfate. The solvent was distilled off under reduced pressure, and the resulting residue was purified by silica gel column chromatography (hexane:ethyl acetate=80:20→50:50, v/v). Thus, the title compound (660 mg, yield: 66%) was obtained.

$^1$H-NMR (400 MHz, CDCl$_3$) δppm: 8.11-8.06 (2H, m), 8.01 (2H, d, J=9 Hz), 8.02-7.96 (1H, m), 7.06 (2H, d, J=9 Hz), 5.52 (1H, t, J=7 Hz), 3.26 (3H, s), 2.95 (2H, q, J=8 Hz), 2.31-2.24 (2H, m), 1.43 (3H, t, J=8 Hz), 1.15 (3H, t, J=7 Hz); MS (FAB$^+$) m/z: 473 [M+H]$^+$.

Formulation Example 5 g of each of the compounds obtained in the Examples, 90 g of lactose, 34 g of corn starch, 20 g of crystalline cellulose, and 1 g of magnesium stearate are mixed with a blender, and then the blend is tabletted with a tabletting machine. Thereby, tablets are obtained.

Test Example 1

Mouse oGTT (Oral Glucose Tolerance Test)

2.0 to 10.0 mg of a test compound was weighed, and then a 0.5 w/v % methyl cellulose solution was added thereto to prepare a liquid for administration at a concentration of 1 mg/ml. Alternatively, 1.0 to 10.0 mg of a test compound was weighed, and then N,N-dimethylformamide was added thereto to prepare a compound solution at a concentration of 20 mg/ml. This was further diluted to 20 times using a 0.5 w/v % methyl cellulose solution, and thereby a liquid for administration at a final concentration of 1 mg/ml was prepared. C57/BL6J mice (male, 6 to 8 weeks old) were purchased from Charles River Laboratories Japan, Inc., and were raised until they were 9 to 13 weeks old. The mice were fasted, starting from a time point between the 17$^{th}$ hour and the 18$^{th}$ hour of the day before the test day. On the test day, blood was collected from the caudal vein, and then the liquid for administration previously prepared was orally administered. Blood was collected again from the caudal vein thirty minutes after the administration (the blood sugar level at this time is designated as a pre-value). Subsequently, a 30% glucose solution was orally administered in an amount of 10 ml/kg, and thereby, the mice were subjected to glucose load. After the glucose load, blood was collected from the caudal vein at time points of 15, 30, 60 and 120 minutes. Each of the collected blood samples was centrifuged to separate blood plasma. The pre-value, and the blood glucose level values at 15, 30, 60 and 120 minutes after the glucose load were measured with a Glucoloader GXT (A&T Corp.) using the separated blood plasma samples, and the decrease rate (%) of the blood sugar level AUC with respect to a vehicle-administered group was calculated. Meanwhile, the vehicle-administered group was administered with a 0.5 w/v % methyl cellulose solution or a 5% v/v N,N-dimethylformamide/0.5 w/v % methyl cellulose mixed solution.

As a result, the compounds of Examples 2, 7, 8, 11 and 22 decreased the AUC by 5% or more and less than 15%, and the compounds of Examples 1, 3 to 6, 18 and 23 decreased the AUC by 15% or more.

Test Example 2

Rat oGTT (Oral Glucose Tolerance Test) and Test for Measuring Compound Concentration in Rat Blood A test compound is weighed, and then a suspension liquid thereof is prepared using a 0.5 w/v % methyl cellulose solution. Zucker Fatty rats and Zucker Diabetic Fatty rats (male, 8 to 20 weeks old) are purchased from Charles River Laboratories Japan, Inc., and before the test, grouping of the rats is carried out on the basis of the blood sugar levels and body weights of the administered groups. The rats are fasted, starting from a time point between the 15$^{th}$ hour and the 18$^{th}$ hour of the day before the test day. On the test day, blood is collected from the caudal vein, and then the suspension liquid previously prepared is orally administered. Blood is collected again from the caudal vein thirty minutes after the administration (the blood sugar level at this time is designated as a pre-value). Subsequently, a 50% glucose solution is orally administered in an amount of 4 ml/kg, and thereby, the rats are subjected to glucose load. After the glucose load, blood is collected from the caudal vein at time points of 30 minutes, 1, 2 and 3 hours. Each of the collected blood samples is centrifuged to separate blood plasma. The pre-value, and the blood glucose level values at 30 minutes, 1, 2 and 3 hours after the glucose load are measured with a Glucoloader GXT (A&T Corp.) using the separated blood plasma samples, and the decrease rate (%) of the blood sugar level AUC with respect to a vehicle-administered group is calculated. Meanwhile, the vehicle-administered group is administered with a 0.5 w/v % methyl cellulose solution.

The blood plasma samples obtained by the method described above are used for the measurement of the plasma concentration of the test compound. In order to measure the plasma concentration of the test compound for a day, blood is collected 4 hours to 8 hours after the administration, and even after 24 hours. The blood plasma is subjected to protein removal, and then is fed to a liquid chromatography/mass analyzer to calculate the compound concentration in the blood plasma.

Test Example 3

Test on Protection of β Cells (Pancreas)

The β cell (pancreas)-protecting action of a test compound can be confirmed by making reference to the method described in Junko Ogawa, et al., Life Sciences, Vol. 65, No. 12, pp. 1287-1296 (1999).

INDUSTRIAL APPLICABILITY

The compound of the present invention or a pharmaceutically acceptable salt thereof is useful as an active ingredient of a pharmaceutical composition for treating and/or preventing type 1 diabetes, type 2 diabetes, gestational diabetes, hyperglycemia due to other factors, impaired glucose tolerance, diabetes-associated diseases, diabetic complications and the like, and protecting β cells or the pancreas.

The invention claimed is:
1. A compound represented by formula (I):

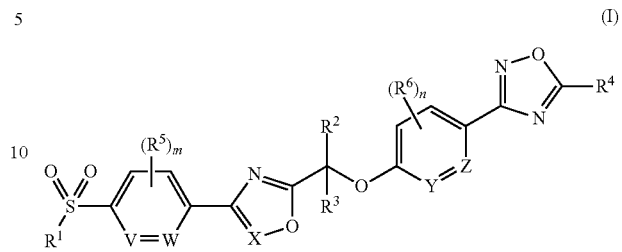

wherein
$R^1$ represents a C1-C6 alkyl group;
$R^2$ and $R^3$ each independently represent a hydrogen atom or a C1-C6 alkyl group;
$R^4$ represents a C1-C6 alkyl group;
$R^5$ and $R^6$ each independently represent a halogen atom or a C1-C6 alkyl group;
m and n each independently represent an integer from 0 to 4;
X is N; and
V, W, Y and Z are CH;
or a pharmaceutically acceptable salt thereof.
2. The compound according to claim 1, wherein $R^1$ represents a C1-C3 alkyl group.
3. The compound according to claim 1, wherein $R^1$ represents a methyl group.
4. The compound according to claim 1, wherein $R^2$ represents a hydrogen atom or a C1-C3 alkyl group.
5. The compound according to claim 1, wherein $R^2$ represents a hydrogen atom, a methyl group, an ethyl group, a propyl group or an isopropyl group.
6. The compound according to claim 1, wherein $R^3$ represents a hydrogen atom or a C1-C3 alkyl group.
7. The compound according to claim 1, wherein $R^3$ represents a hydrogen atom or a methyl group.
8. The compound according to claim 1, wherein $R^4$ represents a C1-C3 alkyl group.
9. The compound according to claim 1, wherein $R^4$ represents an ethyl group, an isopropyl group, or a tert-butyl group.
10. The compound according to claim 1, wherein $R^5$ represents a halogen atom or a C1-C3 alkyl group, and m represents 1.
11. The compound according to claim 1, wherein $R^5$ represents a fluorine atom or a methyl group, and m represents 1.
12. The compound according to claim 1, wherein $R^6$ represents a C1-C3 alkyl group, and n represents 1.
13. The compound according to claim 1, wherein n represents 0.
14. A compound selected from the group consisting of the following compounds:
3-[3-Fluoro-4-methylsulfonyl]phenyl]-5-{1-[4-(5-isopropyl-1,2,4-oxadiazol-3-yl)phenoxy]propyl}-1,2,4-oxadiazole;
3-[3-Fluoro-4-methylsulfonyl]phenyl]-5-{1-[4-(5-isopropyl-1,2,4-oxadiazol-3-yl)phenoxy]ethyl}-1,2,4-oxadiazole;
3-[3-Fluoro-4-(methylsulfonyl)phenyl]-5-{1-[4-(5-isopropyl-1,2,4-oxadiazol-3-yl)phenoxy]butyl}-1,2,4-oxadiazole;
5-Ethyl-3-[4-(1-{3-[3-fluoro-4-(methylsulfonyl)phenyl]-1,2,4-oxadiazol-5-yl}propoxy)phenyl]-1,2,4-oxadiazole;
3-[3-Fluoro-4-(methylsulfonyl)phenyl]-5-{(1R)-1-[4-(5-isopropyl-1,2,4-oxadiazol-3-yl)phenoxy]propyl}-1,2,4-oxadiazole; and 5-Ethyl-3-(4-{[(1R)-1-{3-[3-fluoro-4-(methylsulfonyl) phenyl]-1,2,4-oxadiazol-5-yl}propyl]oxy}phenyl)-1,2, 4-oxadiazole, or a pharmaceutically acceptable salt thereof.

15. A pharmaceutical composition comprising a pharmaceutically acceptable excipient and the compound according to claim 1, or a pharmaceutically acceptable salt thereof.

16. A method for treating type 1 diabetes, type 2 diabetes, or obesity, the method comprising administering to a mammal a pharmacologically effective amount of the compound according to claim 1 or a pharmaceutically acceptable salt thereof.

17. The method according to claim 16, wherein the mammal is a human being.

* * * * *